United States Patent
Schmitt

[11] 3,975,379
[45] Aug. 17, 1976

[54] DIHYDROINDOLES AND INDOLENINE DYESTUFFS

[75] Inventor: Ernst Schmitt, Cologne, Germany

[73] Assignee: Bayer Aktiengesellschaft, Leverkusen, Germany

[22] Filed: May 1, 1974

[21] Appl. No.: 466,052

Related U.S. Application Data

[62] Division of Ser. No. 206,537, Dec. 9, 1971, Pat. No. 3,860,583.

[30] Foreign Application Priority Data

Dec. 9, 1970  Germany............................ 2060614

[52] U.S. Cl. ...................... 260/240 E; 260/240 D; 260/240.6; 260/240.9
[51] Int. Cl.$^2$...................................... C07D 209/04
[58] Field of Search .......... 260/240 D, 240.9, 240 E, 260/240.6

[56] References Cited
UNITED STATES PATENTS

| | | | |
|---|---|---|---|
| 2,639,282 | 5/1953 | Sprague et al. | 260/240.9 X |
| 3,598,596 | 8/1971 | Chapman | 96/120 |
| 3,767,651 | 10/1973 | Chapman | 260/240 E |
| 3,860,583 | 1/1975 | Schmitt | 260/240 G |

OTHER PUBLICATIONS

Chemical Abstracts vol. 77, pp. 76 to 77 (1972) (abstracts no. 128084n, 128085p and 128089t).

*Primary Examiner*—John D. Randolph
*Attorney, Agent, or Firm*—Plumley and Tyner

[57] ABSTRACT

Dihydroindoles of the formula

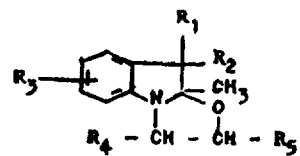

and their use as coupling or condensation components for the manufacture of basic indolenine dyestuffs of the formula

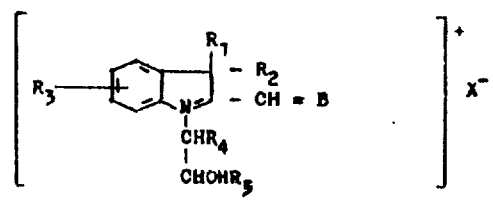

The dyestuffs are used for dyeing and printing natural are used for dyeing and printing natural and synthetic materials.

7 Claims, No Drawings

DIHYDROINDOLES AND INDOLENINE DYESTUFFS

This is a division of application Ser. No. 206,537 filed in the United States, now U.S. Pat. No. 3,860,583 granted Jan. 14, 1975.

The subject of the invention are heterocyclic compounds of the formula

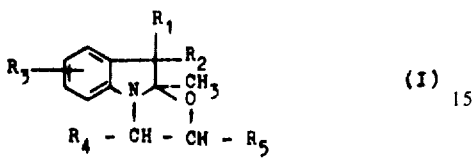

wherein
$R_1$ represents a lower alkyl radical and
$R_2$ represents a lower alkyl radical, and the radicals $R_1$ and $R_2$ together with the shared C atom of the dihydroindole ring can form a saturated 5-membered or 6-membered ring,
$R_3$ represents hydrogen, one or more non-ionic substituents or the remaining part of a fused 5-membered or 6-membered ring which optionally possesses non-ionic substituents, or represents one or more carboxy radicals,
$R_4$ denotes hydrogen or a non-ionic substituent and
$R_5$ denotes hydrogen or a non-ionic substituent,
and a process for their manufacture.

A further subject of the invention are mixtures of these heterocyclic compounds.

The invention also relates to the use of oxazoloindoles as coupling components or condensation components for the manufacture of basic dyestuffs.

A further subject of the invention are basic dyestuffs of the formula

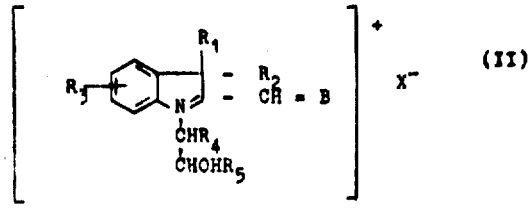

wherein
B represents the groups CH-Ar,

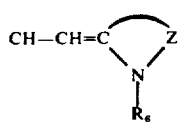

or

$R_1$ represents a lower alkyl radical and
$R_2$ represents a lower alkyl radical, and the radicals $R_1$ and $R_2$ together with the shared C atom of the indolenine ring can form a saturated 5-membered or 6-membered ring,
$R_3$ represents hydrogen, one or more non-ionic substituents or the remaining part of a fused 5-membered or 6-membered ring which optionally possesses non-ionic substituents, or represents one or more carboxy radicals,
$R_4$ denotes hydrogen or a non-ionic substituent,
$R_5$ denotes hydrogen or a non-ionic substituent and
$R_6$ denotes a lower alkyl or aralkyl radical,
Ar represents an aromatic or hetero-aromatic radical which contains at least one donor group which is conjugated with the methine bridge,
Z represents the remaining part of a 5-membered or 6-membered ring to which further rings can be fused,
D represents a carbocyclic or heterocyclic ring with cyclic, planar $(4n+2)$-$\pi$- electron arrangement, to which further rings can be fused, and
$X^-$ represents an anion,
which can be manufactured from 9a-methyl-2,3,9,9a-tetrahydrooxazolo-[3,2a]-indoles.

The invention also relates to mixtures of such basic dyestuffs. A further subject of the invention is the use of these basic dyestuffs for dyeing and printing natural and synthetic materials.

Non-ionic substituents are, for example, alkyl radicals which according to the invention can be cyclic or acyclic, branched or straight-chain, substituted and unsubstituted, such as methyl, ethyl, n-propyl, n-butyl, iso-butyl, tert.-butyl, cyclohexyl, and also higher alkyl radicals, such as n—$C_9H_{19}$ and their substitution products, such as chloromethyl, methoxymethyl, ethoxymethyl, n-propoxymethyl, n-butoxymethyl, n-hexyloxymethyl, n-octyloxymethyl, n-nonyloxymethyl, n-dodecyloxymethyl, aryloxymethyl, such as phenoxymethyl, p-nitrophenoxymethyl, p-methoxyphenoxymethyl and p-chlorophenoxymethyl, β-methoxyethyl, fluorine, chlorine, nitrile, β-cyanoethyl, trifluoromethyl, aryl radicals, especially those of the benzene series, such as phenyl, 2-methylphenyl, 3-methylphenyl, 4-methylphenyl, 2,4-dimethylphenyl, 2-chlorophenyl, 4-chlorophenyl, 2-methyl-4-chlorophenyl, 4-cyanophenyl, 4-nitrophenyl, 4-methoxyphenyl and 4-methylsulphophenyl, aralkyl radicals, especially benzyl and its homologues and their substitution products, such as 4-methylbenzyl, 4-chlorobenzyl, 4-nitrobenzyl, 4-methoxybenzyl and 2-phenylethyl, alkoxy radicals, such as methoxy, ethoxy, n-propoxy and n-butoxy, sulphamoyl radicals, nitrile groups, carboalkoxy radicals, such as carbomethoxy and carboethoxy, and carboaryloxy radicals, such as carbophenoxy and 4-methylcarbophenoxy, and also alkenoxymethyl, such as allyloxymethyl, as well as alkinoxymethyl, such as propargyloxymethyl.

Lower alkyl radicals are those with 1 – 4 carbon atoms, such as methyl, ethyl, n-propyl, iso-propyl, n-butyl, isobutyl, tert.-butyl and their substitution products such as chloromethyl, trifluoromethyl, β-chloroethyl, β-methoxyethyl, β-cyanoethyl and β-dimethylaminoethyl.

Suitable lower alkenyl radicals are, for example: propen-(2)-yl-1, buten-(3)-yl-2 and 2-methylene-propyl-1.

Aralkyl radicals according to the invention are, for example, benzyl, β-phenylethyl, γ-phenylpropyl, phenylpropyl-(2,2), 4-methylbenzyl, 4-chlorobenzyl and 4-nitrobenzyl.

Possible anionic radicals A⁻ are the organic and inorganic anions which are customary for basic dyestuffs and as examples there may be mentioned: chloride, bromide, iodide, carbonate, bicarbonate, $CH_3SO_4^-$, $C_2H_5SO_4^-$, p-toluenesulphonate, $HSO_4^-$, $SO_4^{--}$, disulphate, aminosulphate, methanesulphonate, benzenesulphonate, p-chlorobenzenesulphonate, phosphomolybdate, phosphotungstate, acetate, benzoate, chloroacetate, formate, propionate, lactate, crotonate, $NO_3^-$, perchlorate, $ZnCl_3^-$, the anions of saturated or unsaturated aliphatic dicarboxylic acids, such as malonic acid, maleic acid, tartaric acid, citric acid, oxalic acid, itaconic acid, succinic acid, glutaric acid, adipic acid, pimelic acid and suberic acid, and alkanesulphonic acid radicals, such as n-dodecylsulphonic acid, tetrapropylenesulphonic acids $C_{12}$—$C_{20}$-alkanesulphonic acid mixtures and ligninsulphonic acids.

Colourless anions are preferred; for dyeing from an aqueous medium, those anions which do not excessively impair the solubility of the dyestuff in water are preferred.

For dyeing from organic solvents, those anions are also frequently preferred which assist the solubility of the dyestuff in organic solvents or at least do not affect it adversely, such as anions of monobasic organic acids with 4 – 30 carbon atoms.

Preferred oxazoloindoles of the formula (I) are those of the formula (III)

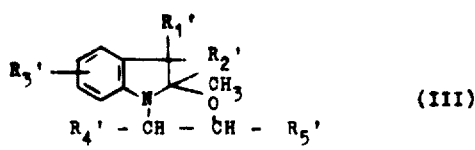

(III)

wherein
$R_1'$ represents methyl, ethyl or n-propyl,
$R_2'$ represents methyl, ethyl or n-propyl,
$R_3'$ represents hydrogen, one or more identical or different radicals from amongst fluorine, chlorine, methyl, ethyl, n-propyl, trifuoromethyl, tert.-butyl, n-hexyl, n-dodecyl, cyclohexyl, phenyl, 4-nitrophenyl, 4-methoxyphenyl, benzyl, methoxy, ethoxy, n-propoxy, n-butoxy, methylmercapto, ethylmercapto, methylsulphonyl, acetamino, phenoxy, carbomethoxy, carboethoxy, carbophenoxy, sulphamoyl, nitrile or carboxyl, and
$R_4'$ and $R_5'$ independently of one another represent hydrogen, methyl, ethyl, n-propyl, n-butyl, n-pentyl, n-hexyl, n-nonyl, chloromethyl, methoxymethyl, ethoxymethyl, n-propoxymethyl, n-butoxymethyl, n-hexyloxymethyl, n-octyloxymethyl, n-nonyloxymethyl, n-dodecyloxymethyl, phenoxymethyl, phenyl, 4-chlorophenyl, 4-nitrophenyl, 4-methoxyphenyl, carbomethoxy, carboethoxy, carbophenoxy, allyloxymethyl, chlorine or nitrile.

Particularly preferred compounds (I) an (III) are those
wherein
$R_4$ and $R_5$ or $R_4'$ and $R_5'$ represent hydrogen or one of the radicals $R_4$ and $R_5$ or $R_4'$ and $R_5'$ represents hydrogen and the other represents a methyl radical, a chloromethyl radical, a phenyl radical, a phenoxymethyl radical, a methoxymethyl radical, an allyloxymethyl radical or a n-hexoxymethyl radical.

For economic reasons, particularly interesting compounds of the formulae (I) an (III) are those,
wherein
$R_4$ and $R_5$ or $R_4'$ and $R_5'$ represent hydrogen, or one of the radicals
$R_4$ and $R_5$ or $R_4'$ and $R_5'$ represents methyl.
Compounds of the formulae (I) and (III)
in which
$R_4$ and $R_5$ or $R_4'$ and $R_5'$ represent hydrogen, are of outstanding importance.

When using unsymmetrical oxiranes, that is to say those exiranes in which the radicals $R_4$ and $R_5$ or $R_4'$ and $R_5'$ are different, oxazoloindole mixtures can be produced.

The conversion of indolenines into indolenium salts by means of alkylating agents, such as dimethyl sulphate and methyl iodide has already been known for a long time. Furthermore, the reaction of 2,3,3-trimethyl-indolenine with 2-bromoethanol to give N-(2-hydroxyethyl)-2,3,3-trimethyl-3-H-indoleninium bromide is known from Belgian patent specification No. 726,639. Furthermore, the use of 1-hydroxyethyl-3,3-dimethyl-2-methylene-indoline and of the corresponding 1-hydroxypropyl and 1-hydroxybutyl compounds as coupling components of basic dyestuffs is known in Belgian patent specification No. 726,639.

It has now been found that, surprisingly, the alkylating reaction of indolenines of the formula

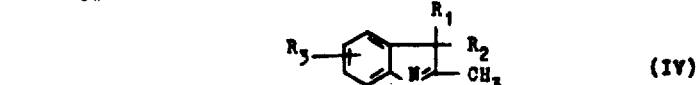

(IV)

wherein
$R_1$ represents a lower alkyl radical and
$R_2$ represents a lower alkyl radical and the radicals $R_1$ and $R_2$ together with the shared C atom of the indolenine ring can form a saturated 5-membered or 6-membered ring,
$R_3$ represents hydrogen, one or more non-ionic sustituents or the remaining part of a fused 5-membered or 6-membered ring which optionally possesses non-ionic substituents, or represents one or more carboxy radicals,
with oxiranes of the formula

(V)

whrerein
R4 denotes hydrogen or a non-ionic substituent and
$R_5$ denotes hydrogen or a non-ionic substituent,
leads simply, and in part with excellent yields, to oxazoloindoles of the formula (I).

The reaction can be carried out in bulk or in the presence of substances which react acid or alkaline, with or without the addition of water. Instead of water, organic solvents can also be used; at times it is useful to use a mixture of water and one or more organic solvents.

Organic acids which are suitable according to the invention are, for example, formic acid, acetic acid, propionic acid, monochloroacetic and dichloroacetic acid, β-chloropropionic acid, succinic acid, benzoic acid and p-toluenesulphonic acid. Organic and inorganic acids can also be used as mixtures; in this case, aqueous hydrochloric acid, sulphuric acid, nitric acid or phosphoric acid are particularly suitable.

Possible substances which give an acid reaction are also Lewis acids, such as $ZnCl_2$, $SnCl_4$, $AlCl_3$, $BF_3$ and $FeCl_3$, which are preferably used together with organic acids, for example those from post-sulphonated styrene-divinylbenzene copolymers.

As organic solvents, the following can, for example, be used: methanol, ethanol, ethylene glycol, benzyl alcohol, acetone, isopropyl methyl ketone, methyl ethyl ketone, cyclohexanol, tetrahydrofurane, dioxane, ethyl acetate, phthalic acid diethyl ester, phthalic acid n-propyl ester, cyclohexane, cyclohexene, benzene, xylenes, chlorobenzene or ethylene chloride.

The reaction is preferably carried out in acetic acid and particularly preferably in acetic acid-water mixtures.

The reaction can be carried out at temperatures between about −20°.and +180°C, preferably at temperatures between 25°C and 80°C. Especially in the case of low-boiling oxiranes, such as ethylene oxide, propylene oxide, butylene-(1,2) oxide and 1-chloro-2,3-epoxypropane, the reaction can advantageously be carried out under pressure.

From amongst the long series of the indolenines which are suitable according to the invention, the following may be mentioned as a selection.

TABLE 1

2,3,3-Trimethyl-indolenine, 2-methyl-3,3-diethylindolenine, 2,3,3,5-tetramethylindolenine, 2,3,3-trimethyl-5-chloro-indolenine, 2,3,3-trimethyl-5-carboxyindolenine, 2,3,3-trimethyl-5-cyclohexyl-indolenine, 2,3,3,7-tetramethyl-5-cyclohexyl-indolenine, 2,3,3-trimethyl-5-trifluoromethylindolenine, 2,3,3-trimethyl-5-methoxyindolenine, 2,3,3-trimethyl-5-sulphamoylindolenine, 2,3,3-trimethyl-5-phthalimidomethyl-indolenine, 2,5-dimethyl-3,3-diethylindolenine, 2-methyl-5-chloro-3,3-diethylindolenine, 2,3,3-trimethyl-5,6-benzo-indolenine, 2,3,3-trimethyl-5-ethoxyindolenine, 2,3,3-trimethyl-5-butoxyindolenine, 2-methyl-3,3-diethyl-5-methoxyindolenine, 2-methyl-3,3-diethyl-5-carboxyindolenine, 2-methyl-3,3-diethyl-5-carbomethoxyindolenine, 2-methyl-3,3-diethyl-5-carboethoxyindolenine, 2,3,3-trimethyl-6-chloroindolenine, 2,3,3-trimethyl-7-chloroindolenine, 2,3,3-trimethyl-5-fluoroindolenine, 2,3,3-trimethyl-5-carbomethoxyindolenine, 2,3,3-trimethyl-5-ethylindolenine, 2,3,3-trimethyl-5-dodecylindolenine, 2,3,3-trimethyl-5-n-butylindolenine, 2,2,3-trimethyl-5-n-propylindolenine, 2,3,3-tirmethyl-5-benzylindolenine, 2-methyl-3,3,5-triethylindolenine, 2-methyl-3,3-diethyl-5-n-propylindolenine, 2-methyl-3,3-diethyl-5-dodecylindolenine, 2,3,3-trimethyl-5-chloro-6-phthalimidomethylindolenine, 2,3,3,5-tetramethyl-6-phthalimidomethylindolenine, 2,3,3-trimethyl-5-hexahydro-phthalimidomethylindolenine, 2,3,3-trimethyl-5-cyanoindolenine, 5-chloro-6-fluoro-2,3,3-trimethylindolenine, 2,3,3-trimethyl-6,7-benzoindolenine, 2,3,3-trimethyl-4,5-benzoindolenine, 2,3,3-trimethyl-5-methylmercaptoindolenine, 2,3,3-trimethyl-5-methylsulphonylindolenine and 2,3,3-trimethyl-5-acetylamino-indolenine.

TABLE 2

Oxiranes which are suitable according to the invention are, for example: ethylene oxide, propylene oxide, butylene(1,2) oxide, butylene-(2,3) oxide, 1-chloro-2,3-epoxypropane, 1-methoxy-2,3-epoxypropane, 1-ethoxy-2,3-epoxypropane, 1-n-propoxy-2,3-epoxypropane, 1-isopropoxy-epoxypropane, 1-n-butoxy-2,3-epoxypropane, 1-isobutoxy-2,3-epoxypropane, 1-tert.-butoxy-2,3-epoxypropane, 1-n-pentoxy-2,3-epoxypropane, 1-isopentoxy-2,3-epoxypropane, 1-n-hexoxy-2,3-epoxypropane, 1-(2′-ethyl-n-hexoxy)-2,3-epoxypropane, 1-n-octyloxy-2,3-epoxypropane, 1-n-nonyloxy-2,3-epoxypropane, 1 n-decyloxy-2,3-epoxypropane, 1-n-undecyloxy-2,3-epoxypropane, 1-n-dodecyloxy-2,3-epoxypropane, 1-n-hexadecyloxy-2,3-epoxypropane, 1-n-octadecyl-2,3-epoxypropane, 1-dimethylamino-2,3-epoxypropane, 1-diethylamino-2,3-epoxypropane, 1-di-n-butylamino-2,3-epoxypropane, 1-phenoxy-2,3-epoxypropane, 1-(p-nitrophenoxy)-2,3-epoxypropane, 1-(p-methylphenoxy)-2,3-epoxypropane, 1-(m-methylphenoxy)-2,3-epoxypropane, 1-(o-methylphenoxy)-2,3-epoxypropane, 1-(nonylphenoxy)-2,3-epoxypropane, 1-(dodecylphenoxy)-2,3-epoxypropane, styrene oxide, allyloxy-2,3-epoxypropane, propargyloxy-2,3-epoxypropane, 2,3-epoxypropanol-(1), 1,2-epoxydecane, 1,2-epoxy-3-(4-methylphenylmercapto)-propane, benzoic acid-2,3-epoxy propyl ester, N-(2,3-epoxypropyl)-pyrrolidine, 3-(diallylamino)-1,2-epoxypropane, 3,3,3-trichloro-1,2-epoxypropane, 3,3,3-trifluoro-1,2-epoxypropane, 3,4-epoxybutene-(1), 1,2-epoxy-3-(4-methylphenyl)-propane and 1,2-epoxy-3-(4-methoxyphenyl)-propane.

Ethylene oxide, propylene oxide, allyloxy-2,3-epoxypropane and phenoxy-2,3-epoxypropane are preferred, and ethylene oxide is particularly preferred.

Surprisingly, oxazoloindoles are suitable condensation components for the manufacture of methine dyestuffs. Furthermore, the oxazoloindoles are, surprisingly, suitable for use as coupling components for the manufacture of hydrazone dyestuffs.

The oxazolo-[3,2a]-indoles obtainable according to the invention can here not only be reacted after prior purification to give methine and hydrazone dyestuffs, but can also be reacted directly from the reaction mixture or after simple removal of the diluent.

When the crude product is used for the manufacture of basic dyestuffs in accordance with the invention, it is of advantage to manufacture the crude product in media containing formic acid or acetic acid, especially if ethylene oxide or propylene oxide are employed.

Methine dyestuffs according to the invention, of the general formula

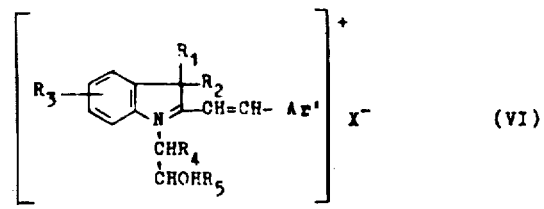

(VI)

wherein
Ar′ represents an aromatic, carbocyclic radical which contains at least one donor group conjugated with the methine bridge,
$R_1$ represents a lower alkyl radical and
$R_2$ represents a lower alkyl radical, and the radicals $R_1$ and $R_2$ together with the shared C atom of the indolenine ring can form a saturated 5-membered or 6-membered ring, $R_3$ represents hydrogen, one or more non-ionic substituents or the remaining part of a fused 5-membered or 6-membered ring which optionally possesses non-ionic substituents, or represents one or more carboxy radicals, $R_4$ denotes hydrogen or a non-ionic substituent, $R_5$ denotes hydrogen or a non-ionic substituent and $X^-$ represents an anion, are manufactured if, in a manner which is in itself known, aromatic formyl compounds of the formula $$OHC - Ar' \qquad (VII)$$

wherein

Ar' has the abovementioned meaning, are condensed with 9a-methyl-2,3,9,9a-tetrahydro-oxazolo-[3,2a]-indoles of the formula

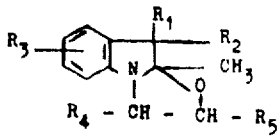

(VIII)

wherein $R_1$ represents a lower alkyl radical and $R_2$ represents a lower alkyl radical, and the radicals $R_1$ and $R_2$ together with the shared C atom of the dihydroindole ring can form a saturated 5-membered or 6-membered ring, $R_3$ represents hydrogen, one or more non-ionic substituents or the remaining part of a fused 5-membered or 6-membered ring which optionally possesses non-ionic substituents, or represents one or more carboxy radicals, $R_4$ denotes hydrogen or a non-ionic substituent and $R_5$ denotes hydrogen or a non-ionic substituent.

Suitable groups Ar according to the invention are those groups of which the carbon atom located in the methine groups is a component of a cyclic planar $(4n+2)$-$\pi$electron system which contains at least one donor group in the o- or p-position which is conjugated with the methine bridge. Aryl groups Ar' are, according to the invention, carbocyclic groups Ar.

Possible donor groups are here above all the groupings -O-R, -S-R and

wherein

R represents an alkyl, aralkyl or aryl radical,

R' represents hydrogen or an alkyl, aralkyl, alkenyl, alkinyl or aryl radical and R'' represents hydrogen or an alkyl, aralkyl, alkenyl, alkinyl or aryl radical, with the proviso that R' and R'' shall not simultaneously denote hydrogen, and wherein these alkyl radicals can optionally be cyclised via further hetero-atoms, such as O, S and NH, N-alkyl, N-aralkyl or N-aryl, and wherein one of the radicals R' and R'' or both radicals can be linked to adjacent ring systems.

Preferred donor groups correspond to the formula

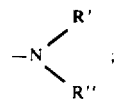

radicals

which are in the p-position to the methine bridge are particularly preferred.

According to the invention, the Ar and Ar' rings defined in more detail above can also contain fused carbocyclic and heterocyclic rings. Possible groups Ar are, for example, optionally substituted, donor-substituted radicals of the benzene, naphthalene, benzofurane, benzothiophene, indole, indoline, 1,2,3,4-tetrahydroquinoline, carbazole, quinoxaline, dihydro-[benzo-1,4-oxazine]-, dihydro-[benzo1,4-thiazine]-, 9,10-dihydro-phenazine-, phenoxazine- and phenthiazine series. According to the invention, those groups of the benzene and naphthalene series in which there is at least one amine-N- grouping in the o- or p-position to the methine group are preferred as groups Ar.

Suitable condensation components of the formula (VII) are, for example:

TABLE 3 p-(N-Dimethylamino)-benzaldehyde, p-(N-diethylamino)benzaldehyde, p-(N-methyl-N-ethylamino)-benzaldehyde, p-(N-methyl-N-$\beta$-cyanoethylamino)-benzaldehyde, p-(N-methyl-N-$\beta$-chloroethylamino-benzaldehyde, 2-methyl-4-(N-ethyl-N-$\beta$-chloroethylamino)-benzaldehyde, 3-formyl-N-ethylcarbazole, 3-formyl-N-methylcarbazole, 3-formyl-N-(n)-butylcarbazole, 4-formyl-N-methyldiphenylamine, 4-formyl-N-methyl-4'-methyldiphenylamine, 4-formyl-4'-methoxy-N-methyldiphenylamine, 4-formyl-4'-ethoxy-N-methyldiphenylamine, 4-formyl-4'-chloro-N-methyldiphenylamine, 4-formyl-2-chloro-N-methyldiphenylamine, 4-(N-piperidinyl)-benzaldehyde, p-(N-di-$\beta$-chloroethylamino)-benzaldehyde, p-(N-ethyl-N-$\beta$-chloroethylamino)-benzaldehyde, p-(N-ethyl-N-$\beta$-cyanoethylamino)-benzaldehyde, p-(N-methyl-N-cyclohexyamino(sic)-benzaldehyde, p-(N-di-n-propylamino)-benzaldehyde, p-(N-n-butyl-N-$\beta$-chloroethylamino)-benzaldehyde, p -[N-ethyl-N-(2'-dimethylaminoethyl)amino]-benzaldehyde, p-(N-ethyl-N-benzylamino)-benzaldehyde, p-(N-ethyl-N-$\beta$-cyanoethylamino)-benzaldehyde, 4-formyl-N-ethyldiphenylamine, 4-formyl-4'-methoxy-N-ethyldiphenylamine, 4-formyl-4'-ethoxy-N-ethyldiphenylamine, 4-formyl-4'-methyl-N-ethyldiphenylamine, 4-formyl-4'-chloro-N-ethyldiphenylamine, N-(p-formylphenyl)-morpholine, 3-formyl-N-(n)-propylcarbazole, 6-formyl-1,2,3,4-tetrahydro-9-ethylcarbazole.

Suitable oxazoloindoles of the formula (VIII) obtainable according to the process of the invention are, for example:

TABLE 4

9,9,9a-Trimethyl-2,3,9,9a-tetrahydro-oxazolo-[3,2a]-indole, 7,9,9,9a-tetramethyl-2,3,9,9a-tetrahydro-oxazolo-[3,2a]-indole, 7-chloro-9,9,9a-trimethyl- 2,3,9,9a-tetrahydro-oxazolo-[3,2a]-indole, 7methoxy-9,9,9a-trimethyl-2,3,9,9a-tetrahydro-oxazolo-[3,2a]-indole, 7-ethyl-9,9,9a-trimethyl-2,3,9,9a-tetrahydro-oxazolo-[3,2a]-indole, 7-cyclohexyl-9,9,9a-trimethyl-2,3,9,9a-tetrahydro-oxazolo-[3,2a]-indole, 7-trifluoromethyl-9,9,9a-trimethyl-2,3,9,9a-tetrahydro-oxazolo-[3,2a]-indole, 7-acetamino-9,9,9a-trimethyl-2,3,9,9a-tetrahydro-oxazolo-[3,2a]-indole, 7-cyclohexyl-5,9,9,9a-tetramethyl-2,3,9,9a-tetrahydro-oxazolo-[3,2a]-indole, 9,9-diethyl-9a-methyl-2,3,9,9a-tetrahydro-oxazolo-[3,2a]-indole, 9,9-diethyl-7,9a-dimethyl-2,3,9,9a-tetrahydro-oxazolo-[3,2a]-indole, 9,9-diethyl-7-chloro-9a-methyl-2,3,9,9a-tetrahydro-oxazolo-[3,2a]-indole, 2,9,9,9a-tetramethyl-2,3,9,9a-tetrahydro-oxazolo-[3,2a]-indole, 3,9,9,9a-tetramethyl-2,3,9,9a-tetrahydro-oxazolo-[3,2a]-indole, 9,9,9a-trimethyl-2-phenoxy-2,3,9,9a-tetrahydro-oxazolo-[3,2a]-indole, 9,9,9a-trimethyl-2-phenoxymethyl-2,3,9,9a-tetrahydro-oxazolo-[3,2a]-indole, 9,9,9a-trimethyl-7-methoxy-2-phenoxymethyl-2,3,9,9a-tetrahydro-oxazolo-[3,2a]-indole, 9,9-diethyl-9a-methyl-2-phenoxymethyl-2,3,9,9a-tetrahydro-oxazolo-[3,2a]-indole, 9,9,9a-trimethyl-2-chloromethyl-2,3,9,9a-tetrahydro-oxazolo-[3,2a]-indole, 9,9,9a-trimethyl-3-chloromethyl-2,3,9,9a-tetrahydro-oxazolo-[3,2a]-indole, 9,9,9a-trimethyl-2-ethyl-2,3,9,9a-tetrahydro-oxazolo-3,2a]-indole, 9,9,9a-trimethyl-7-phthalimidomethyl-2,3,9,9a-tetrahydro-oxazolo-[3,2a]-indole, 9,9,9a-trimethyl-7-cyano-2,3,9,9a-tetrahydro-oxazolo-[3,2a]-indole, 2,9,9,9a-tetramethyl-7-cyano-2,3,9,9a-tetrahydro-oxazolo-[3,2a]-indole, 2,3,9,9,9a-pentamethyl-2,3,9,9a-tetrahydro-oxazolo-3,2a]-indole, 9,9,9a-trimethyl-2-methoxymethyl-2,3,9,9a-tetrahydro-oxazolo-[3,2a]-indole, 5,6-benzo-9,9,9a-trimethyl-2,3,9,9a-tetrahydro-oxazolo-[3,2a]-indole, 6,7-benzo-9,9,9a-trimethyl-2,3,9,9a-tetrahydro-oxazolo-[3,2a]-indole, 6-chloro-9,9,9a-trimethyl-2,3,9,9a-tetrahydro-oxazolo-[3,2a]-indole, 5-chloro-9,9,9a-trimethyl-2,3,9,9a-tetrahydro-oxazolo-[3,2a]-indole, 7-fluoro-9,9,9a-trimethyl-2,3,9,9a-tetrahydro-oxazolo-[3,2a]-indole, 7-chloro-6-fluoro-9,9,9a-trimethyl-2,3,9,9a-tetrahydro-oxazolo-[3,2a]-indole, 7-benzyl-9,9,9a-trimethyl-2,3,9,9 a-tetrahydro-oxazolo-[3,2a]-indole, 7-chloro-2-phenoxymethyl-9,9,9a-trimethyl-2,3,9,9a-tetrahydro-oxazolo-[3,2a]-indole, 7,9,9,9a-tetramethyl-2-phenoxymethyl-2,3,9,9a-tetrahydro-oxazolo-[3,2a]-indole, 7-carboxy-9,9,9a-trimethyl-2,3,9,9a-tetrahydro-oxazolo-[3,2a]-indole, 7-(carbo-β-oxyethoxy)-9,9,9a-trimethyl-2,3,9,9a-tetrahydro-oxazolo-[3,2a]-indole, 7-carboxy-2-phenoxymethyl-9,9,9a-trimethyl-2,3,9,9a-tetrahydro-oxazolo-[3,2a]-indole, 7-carboxy-3-phenoxymethyl-9,9,9a-trimethyl-2,3,9,9a-tetrahydro-oxazolo-[3,2a]-indole, 7-ethoxy-9,9,9a-trimethyl-2,3,9,9a-tetrahydro-oxazolo-[3,2a]-indole, 9,9,9a-trimethyl-2-ethoxymethyl-2,3,9,9a-tetrahydro-oxazolo-[3,2a]-indole, 9,9,9a-trimethyl-2-(n-propoxymethyl)-2,3,9,9a-tetrahydro-oxazolo-[3,2a]-indole, 9,9,9a-trimethyl-2-(n-hexyloxymethyl)-2,3,9,9a-tetrahydro-oxazolo-[3,2a]-indole, 9,9,9a-trimethyl-3-methoxymethyl-2,3,9,9a-tetrahydro-oxazolo-[3,2a]-indole, 9,9,9a-trimethyl-3-ethoxymethyl-2,3,9,9a-tetrahydro-oxazolo-[3,2a]-indole, 9,9,9a-trimethyl-3-(n-hexyloxymethyl)-2,3,9,9a-tetrahydro-oxazolo-[3,2a]-indole, 7,9,9,9a-tetramethyl-2-phenoxymethyl-2,3,9,9a-tetrahydro-oxazolo-[3,2a]-indole, 7-chloro-9,9,9a-trimethyl-2-phenoxymethyl-2,3,9,9a-tetrahydro-oxazolo-[3,2a]-indole,7-fluoro-9,9,9a-trimethyl-2-phenoxymethyl-2,3,9,9a-tetrahydro-oxazolo-[3,2a]-indole, 7-chloro-9,9,9a-trimethyl-2-methoxymethyl-2,3,9,9a-tetrahydro-oxazolo-[3,2a]-indole, 7-chloro-9,9,9a-trimethyl-2-ethoxymethyl-2,3,9,9a-tetrahydro-oxazolo-[3,2a]-indole, 7-chloro-9,9,9a-trimethyl-2-(n-hexyloxymethyl)-2,3,9,9a-tetrahydro-oxazolo-[3,2a]-indole, 7-chloro-9,9,9a-trimethyl-2-(n-propoxymethyl)-2,3,9,9a-tetrahydro-oxazolo-[3,2a]-indole, 7-chloro-2,9,9,9a-tetramethyl-2,3,9,9a-tetrahydro-oxazolo-[3,2a]-indole, 7-chloro-3,9,9,9a-tetramethyl-2,3,9,9a-tetrahydro-oxazolo-[3,2a]-indole, 2,7,9,9,9a-pentamethyl-2,3,9,9a-tetrahydro-oxazolo-[3,2a]-indole, 3,7,9,9a-pentamethyl-2,3,9,9a-tetrahydro-oxazolo-[3,2a]-indole, 7-chloro-2,9,9,9a-tetramethyl-2,3,9,9a-tetrahydro-oxazolo-[3,2a]-indole, 7-chloro-3,9,9,9a-tetramethyl-2,3,9,9a-tetrahydro-oxazolo-[3,2a]-indole, 7-methylmercapto-9,9,9a-trimethyl-2,3,9,9a-tetrahydro-oxazolo-[3,2a]-indole, 7-ethylmercapto-9,9,9a-trimethyl-2,3,9,9,a-tetrahydro-oxazolo-[3,2a]-indole, 7-methylsulphonyl-9,9,9a-trimethyl-2,3,9,9a-tetrahydro-oxazolo-[3,2a]-indole, 9,9,9a-trimethyl-2-allyloxymethyl-2,3,9,9a-tetrahydro-oxazolo-[3,2a]-indole, 9,9,9a-trimethyl-2-n-butoxymethyl-2,3,9,9a-tetrahydro-oxazolo-[3,2a]-indole, 9,9,9a-trimethyl-2-n-decyloxymethyl-2,3,9,9a-tetrahydrooxazolo-[3,2a]-indole and 7,9,9,9a-tetramethyl-6-phthalimidomethyl-2,3,9,9a-tetrahydro-oxazolo-[3,2a]-indole.

The condensation can be carried out by stirring a solution or suspension of equimolar amounts of the compounds (VII) and (VIII) in an organic or inorganic acid, or in a mixture thereof with water, at 10° – 150°C, preferably at 40° – 100°C. Dilute aqueous mineral acids, such as sulphuric acid, phosphoric acid or hydrochloric acid, are for example suitable.

Particularly suitable organic acids are lower fatty acids, such as formic acid, acetic acid, propionic acid and butyric acid. Mixtures of formic acid, acetic acid, propionic acid or butyric acid with fatty acid anhydrides, such as acetic anhydride and propionic anhydride, are also suitable.

The condensation can also be carried out in a solvent, such as, say, benzene, toluene, chlorobenzene, methanol and ethanol, in the presence of acid condensation agents, such as, say, formic acid, acetic acid, propionic acid, butyric acid, phosphorus pentoxide, zinc chloride, aluminium chloride, tin chloride, aqueous sulphuric acid, aqueous phosphoric acid or aqueous hyrochloric acid or their mixtures.

Within the framework of the dyestuffs of the formula (VI), those are particularly preferred,
wherein
$R_3$ represents hydrogen, one or more non-inoic substituents or the remaining part of a fused 5-membered or 6-membered ring which optionally possesses non-ionic substituents,
especially those of the formula

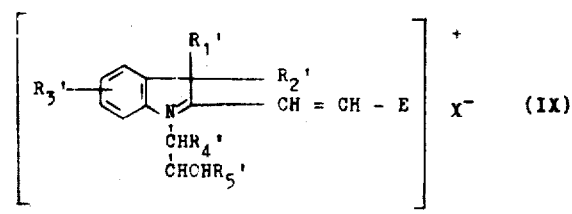

wherein

E represents a carbocyclic, aromatic radical which possesses a

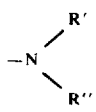

group in the p-position to the methine bridge, wherein

R' represents hydrogen or an alkyl, aralkyl, alkenyl, alkinyl or aryl radical and R'' represents hydrogen or an alkyl, aralkyl, alkenyl, alkinyl or aryl radical, with the proviso that R' and R'' do not simultaneously denote hydrogen, $R_1'$ represents methyl, ethyl or n-propyl, $R_2'$ represents methyl, ethyl or n-propyl, $R_3'$ represents hydrogen or one or more identical or different radicals from amongst methyl, ethyl, fluorine, chlorine, trifluoromethyl, n-propyl, tert.-butyl, n-hexyl, n-dodecyl, cyclohexyl, phenyl,4-nitrophenyl, 4-methoxyphenyl, benzyl, methoxy, ethoxy, n-propoxy, n-butoxy, methylmercapto, ethylmercapto, methylsulphonyl, acetamino, phenoxy, carbomethoxy, carboethoxy, carbophenoxy, sulphamoyl or nitrile, and $R_4'$ and $R_5'$ independently of one another represent hydrogen, methyl, ethyl, n-propyl, n-butyl, n-pentyl, n-hexyl, n-nonyl, chloromethyl, methoxymethyl, ethoxymethyl, n-propoxymethyl, n-butoxymethyl, n-hexoymethyl m-octyloxymethyl, n-nonyloxymethyl, n-dodecyloxymethyl, phenoxymethyl, phenyl, 4-chlorophenyl, 4-nitrophenyl, 4-methoxyphenyl, carbomethoxy, carboethoxy, carbophenoxy or nitrile and $X^-$ represents an anion.

A further outstanding group of methine dyestuffs according to the invention corresponds to the general formula

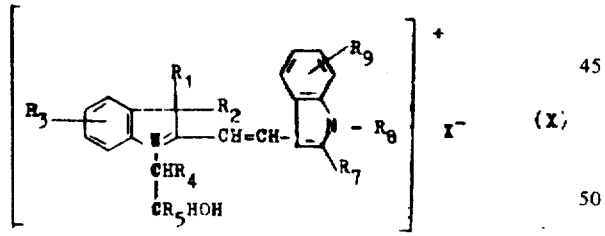

wherein $R_1$ represents a lower alkyl radical and $R_2$ represents a lower alkyl radical, and the radicals $R_1$ and $R_2$ together with the shared bond of the indolenine ring can form a saturated 5-membered or 6-membered ring, $R_3$ represents hydrogen, one or more non-ionic substituents or the remaining part of a fused 5-membered or 6-membered ring which optionally possesses non-ionic substituents, or represents one or more carboxy radical $R_4$ represents hydrogen or a non-ionic substituent $R_5$ represents hydrogen or a non-ionic substituent $R_7$ represents hydrogen, a lower alkyl radical, an aralkyl radical or an aryl radical, $R_8$ represents hydrogen, a lower alkyl radical, a lower alkenyl radical, a lower alkinyl radical or an aralkyl radical, $R_9$ represents hydrogen, a lower alkyl radical, a lower alkoxy radical, an aryl radical, fluorine, chlorine, bromine, nitro, nitrile or the remaining part of a fused 6-membered ring which optionally possesses nonionic substituents, and $X^-$ represents an anion.

Within the framework of the dyestuffs of the formula (X), those are preferred wherein $R_3$ represents hydrogen, one or more non-ionic substituents or the remaining part of a fused 5-membered or 6-membered ring which optionally possesses nonionic substituents.

Dyestuffs of particular importance are those of the formula

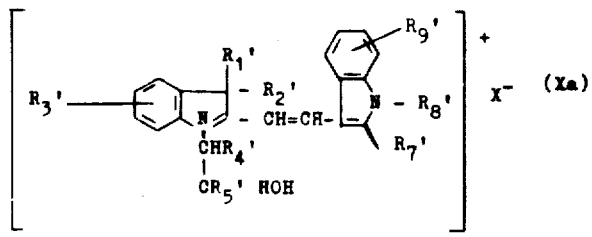

wherein $R_1'$ represents methyl, ethyl or n-propyl, $R_2'$ represents methyl, ethyl or n-propyl, $R_3'$ represents hydrogen, one or more identical or different radicals from amongst methyl, ethyl, n-propyl, fluorine, chlorine, trifluoromethyl, tert.-butyl, n-hexyl, n-dodecyl, cyclohexyl, phenyl, 4-nitrophenyl, 4-methoxyphenyl, benzyl, methoxy, ethoxy, n-propoxy, n-butoxy, methylmercapto, ethylmercapto, methylsulphonyl, acetamino, phenoxy, carboethoxy, sulphamoyl or nitrile, and $R_4'$ and $R_5'$ independently of one another represent hydrogen, methyl, ethyl, n-propyl, n-butyl, n-pentyl, n-hexyl, n-nonyl, chloromethyl, methoxymethyl, ethoxymethyl, n-propoxymethyl, n-butoxymethyl, n-hexyloxymethyl, n-octyloxymethyl, n-nonyloxymethyl, n-dodecyloxymethyl, phenoxymethyl, phenyl, 4-chlorophenyl, 4-nitrophenyl, 4-methoxyphenyl, carbomethoxy, carboethoxy, carbophenoxy, allyloxymethyl, chlorine or nitrile, $R_7'$ represents hydrogen, methyl, ethyl, n-propyl, 4-chlorophenyl, 4-methoxyphenyl or benzyl, $R_8'$ represents hydrogen, methyl, ethyl, n-propyl, isopropyl, n-butyl, iso-butyl or benzyl, $R_9'$ represents hydrogen, methyl, ethyl, chlorine, phenyl or the remaining part of a fused partly or wholly unsaturated carbocyclic 6-membered ring and $X^-$ represents an anion.

Dyestuffs of the formula (X) are obtainable in a surprising manner if, in a manner which is in itself known, indol-3-aldehydes of the formula

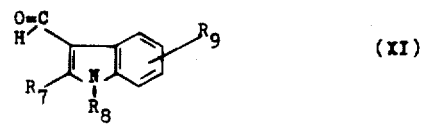

wherein

R₇, R₈ and R₉ have the abovementioned meaning, or functionally similar compounds, are condensed with 9a-methyl-2,3,9,9a-tetrahydroox-azolo-[3,2a]-indoles of the formula (I).

Such functionally similar compounds are, especially, primary products of the Vilsmeier reaction, Schiff's bases, axomethines, oximes, nitrones and hydrazones.

The condensation can be carried out by stirring a solution or suspension of equimolar amounts of the compounds (I) and (XI), or functionally similar compounds, in an organic or inorganic acid or its mixture with water. Temperatures of about 10° to about 150°C, preferably of 40° to 100°C, are chosen as the reaction temperature. Dilute aqueous mineral acids, such as sulphuric acid, phosphoric acid or hydrochloric acid, are for example suitable. Lower fatty acids, such as formic acid, acetic acid, propionic acid and butyric acid, and their mixtures with fatty acid anhydrides, such as acetic anhydride and propionic anhydride, are particularly suitable. The condensation can also be carried out in the presence of an organic solvent, such as benzene, toluene, chlorobenzene, acetonitrile, methanol or ethanol.

Suitable 9a-methyl-2,3,9,9a-tetrahydrooxazolo-[3,2a]-indoles, are, for example, those listed in Table 4. Suitable indol-3-aldehydes are, for example, those listed in the following:

TABLE 5

2-Phenylindol-3-aldehyde, 1-methyl-2-phenylindol-3-aldehyde, 1-methyl-5-methoxy-2-phenylindol-3-aldehyde, 1-methyl-5-chloroindol-3-aldehyde, 1,5-dimethyl-2-phenylindol-3-aldehyde, 2-methyl-7-ethylindol-3-aldehyde, 5-nitro-2-methyl-7-ethylindol-3-aldehyde, 1-ethyl-2-methyl-6,7-benzoindol-3-aldehyde, 1-ethyl-2-phenylindol-3-aldehyde and 2-(4'-chlorophenyl)-7-ethylindol-3-aldehyde.

Dyestuffs of the formula (X), wherein

R₃ represents hydrogen, one or more non-ionic substituents or the remaining part of a fused 5-membered or 6-membered ring which optionally possesses non-ionic substituents, or represents one or more carboxy radicals, and those of the formula (Xa), can be prepared in the same manner.

A further preferred group of methine dyestuffs according to the invention corresponds to the formula

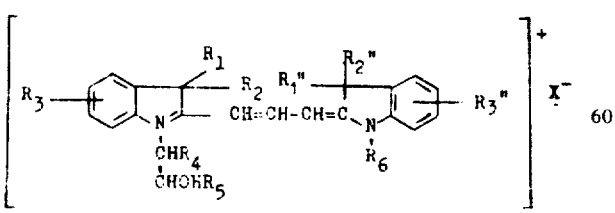

(XII)

wherein $R_1$ represents a lower alkyl radical and $R_2$ represents a lower alkyl radical, and the radicals $R_1$ and $R_2$ together with the shared C atom of the indolenine ring can form a saturated 5-membered or 6-membered ring, $R_1''$ represents a lower alkyl radical, $R_2''$ represents a lower alkyl radical, $R_3$ represents hydrogen, one or more non-ionic substituents or the remaining part of a fused 5-membered or 6-membered ring or represents carboxyl, $R_3''$ represents hydrogen, one or more non-ionic substituents or the remaining part of a fused 5-membered or 6-membered ring or represents carboxyl, $R_4$ denotes hydrogen or a non-ionic substituent, $R_5$ denotes hyrogen or a non-ionic substituent, $R_6$ denotes a lower alkyl or aralkyl radical and $X^-$ denotes an anion .

Dyestuffs of particular importance are those of the formula

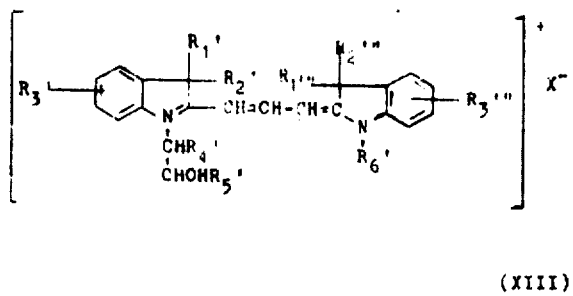

(XIII)

wherein $R_1'$ represents methyl, ethyl or n-propyl, $R_2'$ represents methyl, ethyl or n-propyl, $R_1'''$ represents methyl, ethyl or n-propyl, $R_2'''$ represents methyl, ethyl or n-propyl, $R_3'$ represents hydrogen, methyl, ethyl, fluorine, chlorine, trifluoromethyl, tert.-butyl, cyclohexyl, phenyl, benzyl, methoxy, ethoxy, phenoxy, carboethoxy, sulphamoyl or nitrile, $R_3'''$ represents hydrogen, methyl, ethyl fluorine, chlorine, trifluoromethyl, tert.-butyl, cyclohexyl, phenyl, benzyl, methoxy, ethoxy, methylmercapto, ethylmercapto, methylsulphonyl, phenoxy, carbomethoxy, carboethoxy, sulphamoyl, nitro, amino, acetamino carboxyl or nitrile.

$R_4'$ and $R_5'$ independently of one another represent hydrogen, methyl, ethyl, n-propyl, n-butyl, n-pentyl, n-hexyl, n-nonyl, chloromethyl, methoxymethyl, ethoxymethyl, n-propoxymethyl, n-butoxymethyl, n-hexyloxymethyl, n-octyloxymethyl, n-nonyloxymethyl, n-dodecyloxymethyl, phenoxymethyl, phenyl, 4-nitrophenyl, 4-chlorophenyl, 4-methoxyphenyl, carbomethoxy, carboethoxy, carbophenoxy, allyloxymethyl, chlorine or nitrile, $R_6'$ represents methyl, ethyl, n-propyl or benzyl and $X^-$ represents an anion.

Dyestuffs of the formula XII are manufactured if aldehydes of the formula

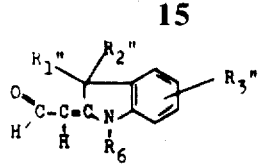

(XIIa)

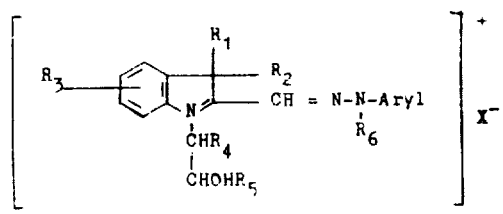

(XIV)

wherein

R$_1''$, R$_2''$, R$_3''$ and R$_6$ have the abovementioned meaning, or functionally equivalent derivatives of these aldehydes, are condensed, in a manner which is in itself known, with 9a-methyl-2,3,9,9a-tetrahydrooxazolo-[3,2a]-indoles of the formula I.

For example, the 9a-methyl-2,3,9,9a-tetrahydrooxazolo-[3,2a]-indoles listed in Table 4 are suitable for this purpose. Suitable aldehyde components are, for example:

TABLE 6

1,3,3-Trimethyl-2-formylmethyleneindoline, 1,3,3-trimethyl-5-chloro-2-formylmethyleneindoline, 1,3,3-trimethyl-5-nitro-2-formylmethyleneindoline, 1,3,3-trimethyl-5-methoxy-2-formylmethyleneindoline, 1,3,3-trimethyl-5-carbomethoxy-2-formylmethyleneindoline, 1,3,3-trimethyl-5-carboethoxy-2-formylmethyleneindoline, 1,3,3,5-tetramethyl-2-formylmethyleneindoline, 1,3,3-trimethyl-5-cyano-2-formylmethyleneindoline, 1,3,3-trimethyl-5-ethyl-2-formylmethyleneindoline, 1,3,3-trimethyl-5-benzyl-2-formylmethyleneindoline, 1-methyl-3,3-diethyl-2-formylmethyleneindoline, 1-methyl-3,3-diethyl-5-chloro-2-formylmethyleneindoline, 1-methyl-3,3-diethyl-5-methoxy-2-formylmethyleneindoline, 1,3,3-trimethyl-6,7-benzo-2-formylmethyleneindoline, 1-ethyl-3,3-dimethyl-2-formylmethyleneindoline, 1,3;3-triethyl-2-formylmethyleneindoline, 1,3,3-trimethyl-5-acetamino-2-formylmethyleneindoline and 1,3,3-trimethyl-5-sulphamoyl-2-formylmethyleneindoline.

Particularly preferred dyestuffs are those of the formulae (VI) to (XII),
wherein
R$_4$ and R$_5$ or R$_4'$ and R$_5'$ represent hydrogen, or wherein one of the radicals R$_4$ and R$_5$ or R$_4'$ and R$_5'$ represents hydrogen and the other represents a methyl radical, a chloromethyl radical, a phenyl radical, a phenoxymethyl radical, a methoxymethyl radical, an allyloxymethyl radical or a n-hexoxymethyl radical.

From an economic point of view, particularly interesting dyestuffs are those of the formulae (VII) to (XII),
wherein
R$_4$ and R$_5$ or R$_4'$ and R$_5'$ represent hydrogen or one of the radicals R$_4$ and R$_5$ or R$_4'$ and R$_5'$ represents methyl.

Compounds of the formulae (VI) and (IX),
wherein
R$_4$ and R$_5$ or R$_4'$ and R$_5'$ represent hydrogen, are of outstanding importance.

The groups of dyestuffs singled out here as being particularly interesting and suitable are also obtainable according to the process of the invention.

Hydrazone dyestuffs according to the invention, of the formula wherein
R$_1$ represents a lower alkyl radical and
R$_2$ represents a lower alkyl radical, and the radicals R$_1$ and R$_2$ together with the shared C atom of the indolenine ring can form a saturated 5-membered or 6-membered ring,
R$_3$ represents hydrogen, one or more non-ionic substituents or the remaining part of a fused 5-membered or 6-membered ring which optionally possesses non-ionic substituents, or represents one or more carboxy radicals,
R$_4$ represents hydrogen or a non-ionic substituent,
R$_5$ represents hydrogen or a non-ionic substituent,
R$_6$ denotes an alkyl, alkenyl or aralkyl radical and
X$^-$ represents an anion,
can be manufactured if azo bases of the formula

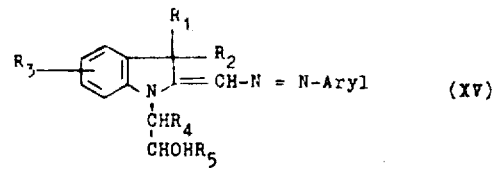

(XV)

wherein
R$_1$, R$_2$, R$_3$, R$_4$ and R$_5$ have the abovementioned meanings,
are reacted with quaternising agents in a manner which is in itself known.

Surprisingly, azo bases of the formula (XV) are obtainable in a manner which is in itself known if amines of the formula $$H_2N - aryl \qquad (XVI)$$

are diazotised and coupled with compounds of the formula

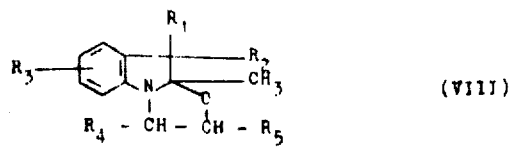

(VIII)

wherein
R$_1$ represents a lower alkyl radical and
R$_2$ represents a lower alkyl radical, and the radicals R$_1$ and R$_2$ together with the shared C atom of the dihydroindole ring can form a saturated 5-membered or 6-membered ring,
R$_3$ represents hydrogen, one or more non-ionic substituents or the remaining part of a fused 5-membered or 6-membered ring which optionally possesses non-ionic substituents, or represents one or more carboxy radicals, $R_4$ denotes hydrogen or a non-ionic substituent and
$R_5$ denotes hydrogen or a non-ionic substituent,
and the coupling product obtained is treated with acid-binding substances, such as, for example, alkali, in a manner which is in itself known.

If mixtures of compounds of the formula VIII are used, mixtures of azo bases are produced.

The alkylation can be carried out by warming the solution or suspension of a compound of the formula (XV) in an inert medium with the alkylating agent to 60° – 150°C, preferably 80° – 120°C. For this purpose, it is also possible to use an excess of the alkylating agent as the solvent.

Suitable inert media are, for example, organic liquids, such as benzine, ligroin, cyclohexane, benzene, toluene, chloroform, chlorobenzene and dichlorobenzene, nitrobenzene, tetralin, dioxane and dimethylformamide.

Suitable alkylating agents are, for example, dimethyl sulphate, diethyl sulphate and di-n-butyl sulphate; benzene-sulphonic acid methyl, ethyl, n-propyl, iso-propyl and iso-butyl esters; toluenesulphonic acid methyl, ethyl, n-propyl, iso-propyl and iso-butyl esters; methyl iodide, ethyl iodide, n-butyl bromide, allyl chloride, allyl bromide, 2-chloro- and 2-bromo-diethyl ether, and also chloro- and bromo-acetic acid esters, such as chloro- and bromo-acetic acid ethyl ester. Dimethyl sulphate is particularly suitable.

The alkylation can also be carried out in the presence of alkaline agents, especially in the presence of tertiary amines which are substituted at the N-atom, in accordance with Belgian patent specification No. 735,565. A particularly suitable amine with bulky substituents is triisopropanolamine Preferred dyestuffs of the formula (XIV) are those, wherein $R_3$ represents hydrogen, one or more non-ionic substituents or the remaining part of a fused 5-membered or 6-membered ring which optionally possesses non-ionic substituents.

Particularly preferred dyestuffs of the formula (XIV) are those, wherein $R_4$ and $R_5$ represent hydrogen or one of the radicals $R_4$ and $R_5$ represents hydrogen and the other represents a methyl radical, a methoxymethyl radical, a n-hexoxymethyl radical, a chloromethyl radical, a phenyl radical, an allyloxymethyl radical or a phenoxymethyl radical.

Dyestuffs of the formula (XIV), wherein $R_4$ and $R_5$ represent hydrogen or one of the radicals $R_4$ and $R_5$ represents hydrogen and the other represents a methyl radical are of outstanding importance. From an economic point of view, dyestuffs of the formula (XIV), wherein $R_4$ and $R_5$ represent hydrogen
are of particular interest.

As examples of suitable amine components of the formula (XVI) there may be mentioned: aniline, p-toluidine, m-toluidine, p-anisidine, m-anisidine, o-anisidine, p-phenetidine, o-phenetidine, 4-amino-acetanilide, N-benzoyl-p-phenylenediamine, 5-amino-2-acetylaminoanisole, 4-amino-2,5-diethoxybenzoic acid anilide, 4-amino-2-methyl-5-methoxybenzanilide, 1-amino-4-ethylbenzene, 1-amino-4-tert.-butylbenzene, 2,4,5-trimethylaniline, 2,3,5-trimethylaniline, 6-amino-3-methoxytoluene, 1-amino-3-chloro-4-methoxybenzene, 1-amino-2,4-dimethoxybenzene, 1-amino-2,5-dimethoxy-benzene, 1-amino-2,4-diethoxybenzene, 1-amino-3,4-dimethoxybenzene, 1-amino-3,4-diethoxybenzene, 2-chloro-4-aminoanisole, 3,4-dicyanoaniline, 4-aminoazobenzene, 4-aminoazotoluene, dehydrothiotoluidine, 4-chloroaniline, 4-fluoroaniline, 2-chloroaniline, 3-chloroaniline, 2,4-dichloroaniline, 2,4-dimethoxy-5-chloroaniline, 4-aminodiphenylmethane, 4-aminodiphenylethane-(1,2), 4-amino-4'-nitrodiphenylmethane, 4,4'-diaminodiphenylmethane, 4-amino-4'-methyldiphenylmethane, 4-amino-4'-hydroxydiphenylmethane, 4-amino-4'-methoxydiphenylmethane, 1,2,3,4-tetrahydro-5-aminonaphthalene, 4-cyclohexylaniline, 2-methyl-4-cyclohexylaniline, 1-aminonaphthlene, 3-amino-N-ethylcarbazole, 4-amino-4'-ethoxy-N-methyldiphenylamine, 4-amino-diphenylene oxide, 3-aminodiphenylene oxide, 3-aminodiphenylene sulphide, 4-aminodiphenyl-ether, 4-amino-4'-methyldiphenylether, 4-aminophenylbenzyl-ether, 4-aminophenyl-α-naphthyl-ether, 4-aminodiphenyl sulphide, 4-amino-4'-methoxydiphenyl-ether, 3-aminophenylbenzyl-ether and 4-aminophenyl-p-chlorobenzyl-ether.

When using oxazolindole mixtures for the manufacture of basic dyestuffs of the formulae VI, IX, X, Xa, XII, XIII and XIV, dyestuff mixtures are produced.

A replacement of dyestuff anions by other dyestuff anions can be carried out according to known processes. For example, the basic dyestuffs can be treated with acid-binding agents, such as sodium carbonate, potassium carbonate, ammonium carbonate, magnesium carbonate, sodium hydroxide, potassium hydroxide, ammonia and silver oxide, optionally in an aqueous medium, whereupon the dyestuff-onium base or the carbinol base are produced, and these can be treated with anion-donating agents, these anions being different from those of the basic dyestuff employed.

The new products (II), (VI), (IX), (X), (Xa), (XII), (XIII) and (XIV) are valuable dyestuffs which can be used for dyeing and printing materials of leather, tannin-treated cotton, cellulose, synthetic polyamides and polyurethanes and for dyeing lignin-containing fibres, such as coir, jute and sisal. They are furthermore suitable for the manufacture of writing fluids, rubber-stamp inks, and ball pen pastes and can also be used in flexographic printing.

Suitable materials for dyeing with the basic dyestuffs of the above general formulae (II), (VI), (X), (Xa), (XII), (XIII) and (XIV) are, in particular, flocks, fibres, filaments, tapes, woven fabrics or knitted fabrics of polyacrylonitrile or of copolymers of acrylonitrile with other vinyl compounds, such as vinyl chloride, vinylidene chloride, vinyl fluoride, vinyl acetate, vinylpyridine, vinylimidazole, vinyl alcohol, acrylic and methacrylic acid esters and amides and asymmetrical dicyanoethylene, or flocks, fibres, filaments, tapes, woven fabrics or knitted fabrics of acid-modified aromatic polyester fibres and acid-modified polyamide fibres.

Acid-modified aromatic polyesters are, for example, polycondensation products of sulphoterephthalic acid and ethylene glycol, that is to say polyethylene glycol terephthalates containing sulphonic acid groups (type DACRON 64 of E. I. DuPont de Nemours and Company), such as are described in Belgian patent specification No. 549,170 and in U.S. Pat. No. 2,893,816.

Dyeing can be effected from a weakly acid liquor, with the goods appropriately being introduced into the dyebath at 40° – 60°C and then dyed at the boil. It is also possible to dye under pressure at temperatures above 100°C. Furthermore, the dyestuffs can be added to spinning solutions for the manufacture of fibres containing polyacrylonitrile or can be applied to the unstretched fibre.

The dyeings of the dyestuffs according to the invention, of the formulae (II), (IV), (IX), (X), (Xa), (XII), (XIII) and (XIV), on materials of polyacrylonitrile or acid-modified polyester fibres are distinguished by very good fastness to light, wet processing, rubbing and sublimation.

With anionic precipitants such as alumina, tannin, phosphotungstic acid and phosphomolybdic acid the dyestuffs form light-fast pigments which can advantageously be employed in paper printing.

The dyestuffs can be used individually or as mixtures. They are very suitable for dyeing shaped articles of polymers or copolymers of acrylonitrile, asymmetrical dicyanoethylene, acid-modified aromatic polyesters or acid-modified synthetic polyamides in chlorinated hydrocarbons as the dyebath, provided they possess substituents, such as, for example, the tert.-butyl group, which assist the solubility in chlorinated hydrocarbons, or provided the anion X⁻ is the anion of a monobasic, organic acid with 4 – 30 carbon atoms.

Examples of such organic acids are: 2-ethylenecaproic acid, lauric acid, oleic acid, linoleic acid, a mixture of aliphatic carboxylic acids with 15–19 carbon atoms (Versatic Acid 1519), a mixture of aliphatic carboxylic acids with 9–11 carbon atoms (Versatic Acid 911), coconut fatty acid first runnings, tetradecanoic acid, undecylenoic acid, dimethylpropanoic acid, dimethylacetic acid, carboxylic acids of which the carbon chain is interrupted by heteroatoms, such as nonylphenol-tetraethylene-glycol-etherpropionic acid, nonylphenoldiethylene-glycol-etherpropionic acid, dodecyltetraethylene-glycol-ether-pripionic acid, 3-(nonyloxy)-propionic acid, 3-(isotridecyloxy)-propionic acid, 3-(isotridecyloxy)-diethylene-glycol-ether-propionic acid, 3-(isotridecyloxy)-diethylene-glycol-ether-propionic acid, ether-propionic acid of the alcohol mixture with 6–10 carbon atoms, nonylphenoxyacetic acid, aromatic carboxylic acids, such as tert.-butyl-benzoic acid, cycloaliphatic carboxylic acids, such as hexahydrobenzoic acid, cyclohexenecarboxylic acid and abietic acid, and sulphonic acid, such as tetrapropylenebenzenesulphonic acid.

Dyestuffs in which the anion A⁻ is the anion of one of the acids listed here are particularly preferred.

If the dyestuffs according to the invention are in the form of salts of the monobasic organic acids with 4 – 30 carbon atoms which have been mentioned, concentrated solutions of good stability of these dyestuffs in chlorinated hydrocarbons can be manufactured, if appropriate with the addition of polar organic solvents which are completely miscible with chlorinated hydrocarbons, such as butyrolactone, dimethylformamide, methanol, dioxane, acetonitrile, methyl ethyl ketone, nitrobenzene, dimethylsulphoxide, benzonitrile and 2-nitrochlorobenzene.

To manufacture such solutions, the dyestuffs according to the invention, in the form of the free bases or carbinol bases, or as salts of organic acids with 4 – 30 carbon atoms, are stirred with chlorinated hydrocarbons and monobasic organic acids with 4 – 30 carbon atoms, if appropriate with the addition of polar organic solvents which are completely miscible with chlorinated hydrocarbons, and if necessary at elevated temperature.

The advantage of the present invention is in particular that it proposes a new way of preparing basic dyestuffs of high value, via the alkylating reaction of indolenines with oxiranes, condensation or coupling — in the case of hydrazone dyestuffs — conversion into the azo base and alkylation and, if desired, anion exchange. The alkylating reaction of indolenines with extremely cheap oxiranes such as ethylene oxide and propylene oxide furthermore makes the process a particularly great technical advance.

EXAMPLE 1

Ethylene oxide is passed into a mixture of 80 g of 2,3,3-trimethylindolenine and 400 g of glacial acetic acid at 40°–45°C for 3½ hours. The reaction mixture is then introduced into 2,000 ml of ice/water and rendered alkaline with concentrated sodium hydroxide solution. The oil which has separated out is taken up in 300 ml of ligroin. The ligroin phase is dried with Na₂SO₄, the ligroin is evaporated off and the residue is distilled to yield 74 g of a liquid which passes over at 78° – 80°C and 0.1 mm Hg, of the formula

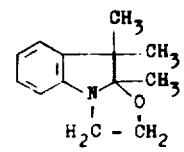

which crystallises to give a colourless substance of melting point: 44° – 46°.

| Analysis | C | H | N | O |
|---|---|---|---|---|
| calculated: | 76.8 | 8.4 | 6.9 | 7.9 |
| found: | 76.1 | 8.6 | 6.9 | 8.2 |

EXAMPLE 2

If ethylene oxide is passed into a mixture of 80 g of 2,3,3-trimethylindolenine and 300 g of glacial acetic acid at 60° – 65°C for 6 hours, working up analogously to Example 1 yields 76.7 g of the reaction product, passing over at 90° – 92°C and 0.3 mm Hg, the constitution of which has been indicated in Example 1.

EXAMPLE 3

If ethylene oxide is passed into a mixture of 80 g of 2,3,3-trimethylindolenine, 90 g of glacial acetic acid and 210 g of water at 45°C for 6 hours, working up analogously to Example 1 yields 78.6 g of the reaction product which passes over at 87°C and 0.2 mm Hg and has the constitution indicated in Example 1.

EXAMPLE 4

60 g of propylene oxide are added dropwise over the course of 3 hours to a mixture of 45 g of 2,3,3-trimethylindolenine and 300 g of glacial acetic acid at 50°C, whilst stirring. The reaction mixture is stirred for a further 2 hours at 50°C and is introduced into approx. 3,000 ml of ice/water, the whole is rendered alkaline with concentrated sodium hydroxide solution and the oil which has separated out is taken up in twice 300 ml of ligroin. After drying with Na₂SO₄ and evaporating off the ligroin, a residue remains from which, after fractional distillation, 13.8 g of the reaction product, passing over as a light yellow oil at 95° – 100°C and 0.3 mm Hg, are obtained. The product corresponds to an approximate composition of:

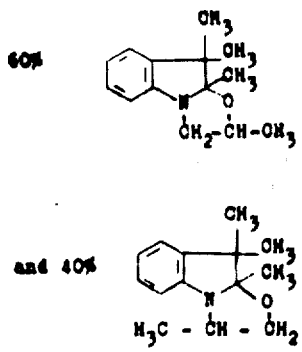

| Analysis: | C | H | N | O |
|---|---|---|---|---|
| calculated: | 77.4 | 8.8 | 6.4 | 7.4 |
| found: | 77.3 | 8.9 | 6.7 | 7.9 |

EXAMPLE 5

50 g of epichlorohydrin are added dropwise over the course of 4 hours to a mixture of 80 g of 2,3,3-trimethylindolenine and 300 g of glacial actic acid at 60°C, whilst stirring, and the mixture is then stirred for a further 2 hours at 80°C. It is then poured into 2,000 g of ice/water and carefully rendered alkaline with sodium hydroxide solution, whilst keeping the mixture at 0°C, and the oil which separates out is taken up in twice 200 ml of ligroin. After evaporating off the ligroin, an oil remains, from which 31.5 g of the liquid reaction product, passing over at 116°– 125°C and 0.3 mm Hg, are obtained after fractional distillation. Composition: mixture of

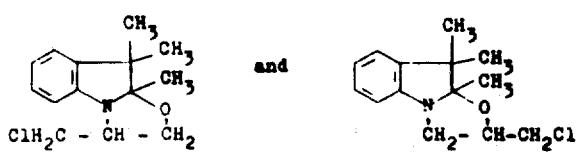

| Analysis: | C | H | N | O | Cl |
|---|---|---|---|---|---|
| calculated: | 66.8 | 7.2 | 5.6 | 6.3 | 14.1 |
| found: | 66.6 | 7.2 | 5.5 | 7.0 | 13.8 |

EXAMPLE 6

70 g of styrene oxide are added dropwise over the course of 1½ hours to a mixture of 80 g of 2,3,3-trimethylindolenine and 300 g of glacial acetic acid at 80°C and the mixture is then stirred for a further hour at 80°C. The reaction mixture is introduced into 1,500 ml of ice/water, then rendered alkaline with concentrated sodium hydroxide solution and treated with 400 ml of benzene. The residue which remains on evaporating off the benzene phase after fractional distillation yields 10.6 g of the reaction product which passes over at 155°– 160°C and 0.2 mm Hg. Composition: mixture of

EXAMPLE 7

80 g of phenoxypropylene oxide are added dropwise over the course of 2 hours to a mixture of 80 g of 2,3,3-trimethylindolenine and 300 g of glacial acetic acid at 80°C, whilst stirring, and the mixture is subsequently stirred for a further 2 hours at 80°C. The reaction mixture is introduced into 1,500 g of ice/water and rendered alkaline with concentrated sodium hydroxide solution, and the oil which has separated out is taken up in 400 ml of benzene. The benzene phase is dried with Na₂SO₄ and thereafter, following evaporation of the benzene, the residue is distilled under reduced pressure. 33.7 g of the reaction product, which passes over at 150°–162°C and 0.1 mm Hg and solidified on cooling, are obtained:
Melting point: 64°– 68°C.
Composition: mixture of

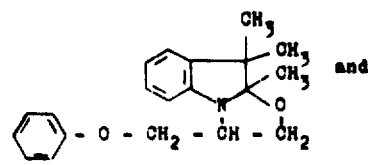

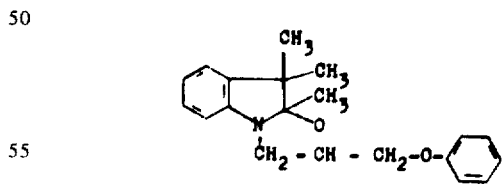

| Analysis: | C | H | N | O |
|---|---|---|---|---|
| calculated: | 76.8 | 7.7 | 4.7 | 10.8 |
| found: | 77.8 | 7.9 | 4.6 | 10.9 |

EXAMPLE 8

20 g of 5-cyclohexyl-2,3,3,7-tetramethylindolenine in 130 g of glacial acetic acid are reacted with ethylene oxide for 2½ hours at 35+C. The reaction mixture is worked up analogously to Example 7. Hereupon, 10.2 g of the reaction product which passes over at 130°C and 0.1 mm Hg and is viscous at room temperature, of the constitution

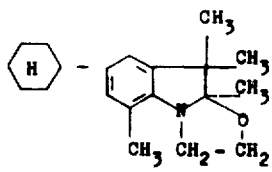

are obtained.

EXAMPLE 9

Ethylene oxide is passed into a mixture of 60 g of 5-methoxy-2,3,3-trimethylindolenine and 300 g of glacial acetic acid at 40°C for 5 hours, whilst stirring. Working up takes place analogously to Example 7. Hereupon, 29.5 g of the reaction product are obtained as an oil which passes over at 104°–108°C and 0.1 mm Hg and is viscous at room temperature.

Constitution:

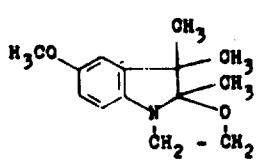

| Analysis: | C | H | N | O |
|---|---|---|---|---|
| calculated: | 72.1 | 8.2 | 6.0 | 13.7 |
| found: | 71.8 | 8.5 | 6.2 | 13.8 |

EXAMPLE 10

Ethylene oxide is passed through a solution of 20 g of 5-(phthalimidomethylene)-2,3,3-trimethylindolenine in 250 g of glacial acetic acid at 40°C for 5 hours. The reaction mixture is then introduced into 1,500 ml of ice/water and carefully rendered alkaline with sodium hydroxide solution whilst maintaining a temperature of approx. 0°C. The solid product which precipitates is washed with water until neutral and then recrystallised from dimethylformamide.

Yield: 8.5 g; Melting point: 197°–198°C.

Constitution:

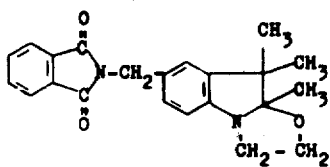

| Analysis: | C | H | N | O |
|---|---|---|---|---|
| calculated: | 72.9 | 6.1 | 7.7 | 13.3 |
| found: | 72.3 | 6.3 | 8.0 | 14.3 |

EXAMPLE 11

16 g of phenoxypropylene oxide are added dropwise over the course of 1 hour to a solution of 20 g of 2,3,3-trimethyl indolenine-5-carboxylic acid in 100 g of glacial acetic acid at 60°C, whilst stirring. The reaction mixture is stirred for a further hour at 80°C, introduced into 600 g of ice/water and rendered alkaline with 20% strength sodium hydroxide solution, whereupon the product dissolves apart from a small proportion of oil. The solution is treated with charcoal and filtered, and the filtrate is adjusted to pH 5 – 6 whilst keeping the temperature at 0°C. Hereupon the reaction product precipitates as a lumpy mass. This is then again stirred with 250 ml of 5% strength sodium hydroxide solution for 3 hours at 60°C; after treatment with charcoal, the filtrate is adjusted to pH 5 – 6 with concentrated hydrochloric acid whilst cooling to 0°C. The mass which precipitates in a flocculent form and is almost colourless is recrystallised from methanol/water (5 : 1).

Melting point: 181° – 183°C.

Constitution: mixture of

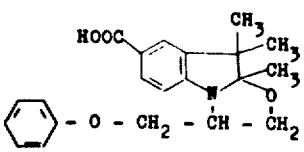

and

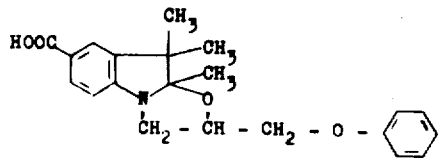

| Analysis: | C | H | N | O |
|---|---|---|---|---|
| calculated: | 71.4 | 6.5 | 4.0 | 18.1 |
| found: | 70.5 | 6.7 | 4.0 | 18.2 |

EXAMPLE 12

40 g of 1-(n)-hexyloxy-2,3-epoxypropane are added dropwise over the course of 2 hours to a solution of 40 g of 2,3,3-trimethylindolenine in 250 ml of glacial acetic acid at 120°C. The mixture is stirred for a further hour at 120°, a further 10 g of 1-(n)-hexyloxy-2,3-epoxypropane are added dropwise at 120°, and the whole is again stirred for a further 2 hours at 120°. The reaction mixture is then introduced into 1,500 ml of ice/water and rendered alkaline with sodium hydroxide solution at 0°C, and the oil which separates out is taken up in benzene. After drying the benzene phase with $Na_2SO_4$ and distilling off the benzene, an oil remains, which is fractionated at 0.1 mm Hg. Hereupon, the reaction product passes over at 135°–145° and 0.1 mm Hg, as a mixture of the two components:

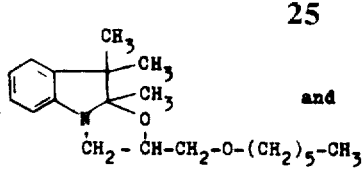

and

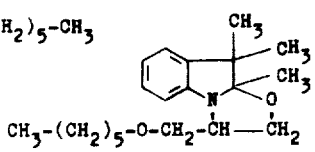

| Analysis: | C | H | N | O |
|---|---|---|---|---|
| calculated: | 75.7 | 9.8 | 4.4 | 10.1 |
| found: | 74.9 | 9.9 | 4.5 | 10.9 |

EXAMPLE 13

60 g of glycidallyl-ether are added dropwise over the course of 2 hours to a mixture of 80 g of 2,3,3-trimethylindolenine and 300 ml of glacial acetic acid at 80°C, the mixture is stirred for a further hour at 80°C, a further 20 g of glycidallyl-ether are added dropwise over the course of 1 hour at 100°C, and the whole is stirred for a further hour at 100°C. The reaction mixture is then introduced into 2 kg of ice water and is rendered alkaline with sodium hydroxide solution, and the oil which has separated out is taken up in ligroin and fractionated after evaporating off the solvent. 69.4 g of a colourless oil, which passes over at 155°C and 1.5 mm Hg, is obtained as a mixture of the following two components:

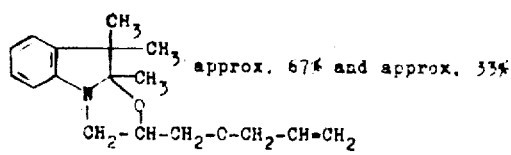

| Analysis: | C | H | N | O |
|---|---|---|---|---|
| calculated: | 74.8 | 8.4 | 5.1 | 11.7 |
| found: | 72.8 | 8.5 | 5.6 | 11.7 |

EXAMPLE 14

9.2 g of p-anisidine are dissolved in a mixture of 24 ml of 30% strength aqueous hydrochloric acid and 300 ml of water and diazotised with 30% strength aqueous sodium nitrite solution at 0°C. After destroying excess nitrite by adding amidosulphonic acid, 15.3 g of the substance obtained according to Example 1 are added dropwise over the course of 1½ hours at 0° - 5°C. The mixture is then neutralised to pH 5 over the course of 4 hours by means of 20% strength sodium acetate solution, the temperature rising to 15°C towards the end. The pH is then adjusted to 9 with 10% strength sodium hydroxide solution and the mixture is stirred for 15 hours at room temperature. The product which precipitates is filtered off, washed with water until neutral, dried in vacuo at 60°C and recrystallised from methanol with the addition of charcoal.

Red crystals of melting point: 129° – 130°C; Yield: 17.6 g.

For the alkylation, 15.2 g of azo base in 100 ml of anhydrous chlorobenzene are treated with 1.0 g of triisopropanolamine and then reacted with 8.7 g of dimethyl sulphate for 6 hours at 80°C. The chlorobenzene is then removed by steam distillation and the crude product which precipitates is purified by recrystallisation from water with the addition of charcoal. The dyestuff of the formula

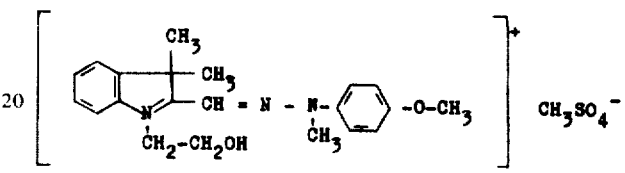

which is obtained in yellow crystals dyes materials of polyacrylonitrile in reddish-tinged yellow shades of good fastness to light and to wet processing.

EXAMPLe 15

14 g of 3-amino-N-ethylcarbazole are diazotised, in a mixture of 200 ml of water and 16 ml of 30% strength aqueous hydrochloric acid, with 30% strength aqueous sodium nitrite solution at 10°C. The diazonium solution obtained after destroying excess nitrite and after filtration is treated dropwise over the course of 1 hour, at approx. 10°C, with 11.7 g of the product obtained according to Example 9. The mixture is then neutralised to pH 5 over the course of 5 hours by means of 20% strength aqueous sodium acetate solution, the temperature rising to approx. 20°C towards the end. The azo base liberated by adding alkali is filtered off, washed with water until neutral and dried in vacuo at 60°C. Yield: 20.7 g; Melting point: 127° – 130°C (benzene/ligroin).

For the alkylation, 12 g of the azo base in 100 ml of anhydrous chlorobenzene are treated with 1.0 g of triisopropanolamine and then reacted with 4.8 g of dimethyl sulphate at 80° - 85°C for 6 hours. The residue which remains after removing the chlorobenzene is recrystallised from water after addition of charcoal. The dyestuff of the formula

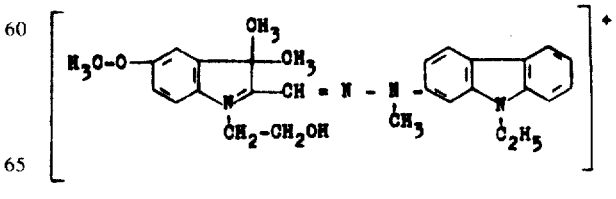

is obtained as red-violet crystals and dyes fabrics of polyacrylonitrile in red-violet shades of good fastness to light and to wet processing.

If the starting components listed in the table which follows are used for the manufacture of the azo bases, alkylation with dimethyl sulphate yields dyestuffs which dye fabrics of polyacrylonitrile in the colour shades indicated.

| Amine Component | Coupling Component | Colour shade |
|---|---|---|
| aniline | according to Example 1 | yellow |
| p-toluidine | '' | yellow |
| p-anisidine | '' | reddish-tinged yellow |
| 1-amino-3,4-dimethoxybenzene | '' | orange |
| 1-amino-3,4-di-isopropoxybenzene | '' | orange |
| 1-amino-4-acetylaminobenzene | '' | orange |
| 1-amino-4-chlorobenzene | '' | yellow |
| o-anisidine | '' | yellow |
| 4-ethylaniline | '' | yellow |
| 4-benzylaniline | '' | reddish-tinged yellow |
| p-phenetidine | '' | reddish-tinged yellow |
| 4-tert.-butylaniline | '' | yellow |
| 4-aminodiphenyl-ether | '' | reddish-tinged yellow |
| 3-aminodiphenyl-ether | '' | yellow |
| 4-aminobenzophenone | '' | reddish-tinged yellow |
| 4-amino-4'-methylbenzophenone | '' | reddish-tinged yellow |
| 3-aminobenzophenone | '' | reddish-tinged yellow |
| 4-aminoazobenzene | '' | orange |
| 3-aminodiphenylene oxide | '' | reddish-tinged yellow |
| dehydrothiotoluidine | '' | orange |
| 3-amino-N-ethylcarbazole | '' | red |
| 3-amino-N-methylcarbazole | '' | red |
| 4-cyclohexylaniline | '' | yellow |
| 4-amino-4'-nitrodiphenylmethane | '' | reddish-tinged yellow |
| p-toluidine | according to Example 10 | yellow |
| p-toluidine | 7-chloro-9,9,9a-trimethyl-2,3,9,9a-tetrahydrooxazolo-[3,2a]-indole | yellow |
| p-anisidine | '' | reddish-tinged yellow |
| 4-benzylaniline | '' | reddish-tinged yellow |
| 1-amino-3,4-dimethoxybenzene | '' | orange |
| 1-amino-4-chlorobenzene | '' | yellow |
| 4-aminobenzophenone | '' | reddish-tinged yellow |
| 3-amino-4-methylbenzophenone | '' | yellow |
| 4-aminodiphenyl-ether | '' | reddish-tinged yellow |
| 4-aminoazobenzene | '' | orange |
| 3-amino-N-ethylcarbazole | '' | red |
| 4-cyclohexylaniline | '' | yellow |
| α-naphthylamine | '' | reddish-tinged yellow |
| 2-aminodiphenyl oxide | '' | reddish-tinged yellow |
| phenyl-(4-aminobenzyl)-sulphone | '' | reddish-tinged yellow |
| tetrahydro-α-naphthylamine | '' | yellow |
| p-anisidine | according to Example 13 | reddish-tinged yellow |
| 4-aminodiphenylmethane | '' | reddish-tinged yellow |
| aniline | '' | yellow |
| p-anisidine | 7-methyl-9,9,9a-trimethyl-2,3,9,9a-tetrahydrooxazolo-[3,2a]-indole | reddish-tinged yellow |
| p-anisidine | 7-trifluoromethyl-9,9,9a-trimethyl-2,3,9,9a-tetrahydrooxazolo-[3,2a]-indole | reddish-tinged yellow |
| 3-amino-N-ethylcarbazole | '' | red |
| α-naphthylamine | according to Example 1 | reddish-tinged yellow |
| tetrahydro-α-naphthylamine | '' | yellow |
| 4-aminodiphenyl sulphide | '' | yellow |
| 4-amino-4'-methoxydiphenyl-methane | '' | reddish-tinged yellow |
| 4-amino-4'-nitrodiphenyl-methane | according to Example 5 | reddish-tinged yellow |
| p-toluidine | according to Example 9 | reddish-tinged yellow |
| p-anisidine | '' | orange |
| 3-amino-N-ethylcarbazole | '' | bluish-tinged-red |
| p-toluidine | according to Example 7 | yellow |
| p-anisidine | '' | reddish-tinged yellow |
| p-phenetidine | '' | reddish-tinged yellow |
| aniline | '' | yellow |
| p-toluidine | according to Example 12 | yellow |
| aniline | '' | yellow |
| 4-aminodiphenylmethane | '' | yellow |
| p-toluidine | according to Example 8 | yellow |
| 4-aminodiphenylmethane | '' | yellow |
| p-toluidine | 7-cyclohexyl-9,9,9a-trimethyl-2,3,9,9a-tetrahydrooxasolo-[3,2a]-indole | yellow |
| 4-aminodiphenylmethane | '' | reddish-tinged yellow |
| p-anisidine | '' | reddish-tinged yellow |
| 4-amino-4'-methyldiphenyl-methane | '' | reddish-tinged yellow |
| 3-amino-N-ethylcarbazole | '' | red |
| p-anisidine | 7-fluoro-9,9,9a-trimethyl-2,3,9,9a-tetrahydrooxazolo-[3,2a]-indole | reddish-tinged yellow |
| p-toluidine | '' | yellow |
| 3-amino-N-methylcarbazole | '' | red |
| 3-aminobenzophenone | '' | yellow |
| p-anisidine | 5-chloro-9,9,9a-trimethyl-2,3,9,9a-tetrahydrooxazolo-[3,2a]-indole | reddish-tinged yellow |
| 4-amino-4'-nitrodiphenyl-methane | '' | reddish-tinged yellow |

| Amine Component | Coupling Component | Colour shade |
|---|---|---|
| 4-amino-4'-nitrodiphenyl-methane | according to Example 6 | reddish-tinged yellow |
| p-anisidine | '' | reddish-tinged yellow |
| p-toluidine | according to Example 11 | reddish-tinged yellow |

EXAMPLE 16

4 g of the reaction product obtained in Example 1 and 5 g of 4-formyl-4'-ethoxy-N-methyldiphenylamine in a mixture of 35 g of glacial acetic acid and 2 g of acetic anhydride are heated for 5 hourst to 85° - 90°C. The reaction mixture is then introduced into 200 ml of 10% strength aqueous sodium chloride solution and is stirred for 24 hours at room temperature. The dyestuff which precipitates is filtered off, washed with 5% strength aqueous sodium chloride solution and dried in vacuo at 45°C. The resulting dyestuff of the formula 25 ml of glacial acetic acid and 3 ml of acetic anhydride are stirred for 6 hours at 90° - 100°C. The reaction mixture is then introduced into 100 ml of 10% strength aqueous sodium chloride solution and stirred for 24 hours at room temperature, and the mass which precipitates is purified by reprecipitation from water/10% strength sodium chloride solution/charcoal. The dyestuff obtained dyes fabrics of polyacrylonitrile in violet shades.

It is probably a mixture corresponding to the formulae

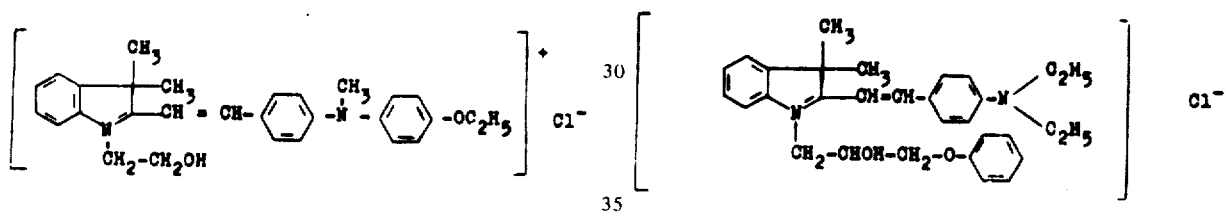

and dyes fabrics of polyacrylonitrile in violet-red shades of high fastness to light and to wet processing.

EXAMPLE 17

6 g of the reaction product obtained in Example 1 are heated with 3-formyl-N-ethylcarbazole in a mixture of 50 ml of glacial acetic acid and 1.5 ml of acetic anhydride for 7 hours to 90°C. The reaction mixture is poured into 200 ml of 10% strength aqueous sodium chloride solution and stirred for 24 hours. The crude dyestuff of the formula

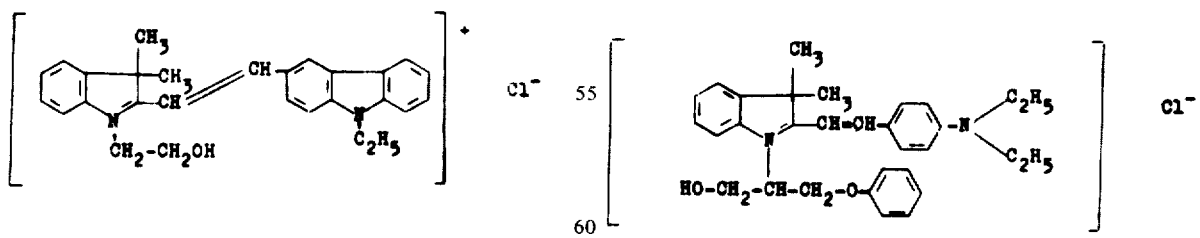

which precipitates is reprecipitated from water/5% strength sodium chloride solution. It is obtained as greenish glistening crystals and dyes fabrics of polyacrylonitrile in luminous scarlet red shades.

EXAMPLE 18

3.1 g of the reaction product obtained in Example 7 and 1.9 g of diethylaminobenzaldehyde in a mixture of If the starting components listed in Table 2 below are used for the condensation and the instructions given in Examples 14 – 17 are followed, dyestuffs are obtained which dye fabrics of polyacrylonitrile in the colour shades indicated.

Table 2

| Carbonyl Component | Oxazoloindole Derivative | Colour shade |
|---|---|---|
| 4-dimethylaminobenzaldehyde | according to Example 1 | brilliant bluish-tinged red |
| 2-methyl-N-ethyl-N-β-chloro-ethylaminobenzaldehyde | " | clear bluish-tinged red |
| 4-(N-methyl-N-β-cyanoethyl)-amino-benzaldehyde | " | rose |
| 3-formyl-N-ethylcarbazole | according to Example 4 | red |
| 3-formyl-N-ethylcarbazole | according to Example 5 | scarlet |
| 4-(N-methyl-N-β-cyanoethyl)-amino-benzaldehyde | " | bluish-tinged red |
| 3-formyl-N-ethylcarbazole | according to Example 7 | brilliant red |
| 4-diethylaminobenzaldehyde | " | violet |
| 3-formyl-N-ethylcarbazole | according to Example 9 | red |
| 4-diethylaminobenzaldehyde | according to Example 10 | violet |
| 4-(N-methyl-N-β-cyanoethyl)-amino-benzaldehyde | according to Example 11 | red-violet |

EXAMPLE 19

A mixture of 4.1 g of the product obtained according to Example 1 and 3.2 g of 2-methylindole-3-aldehyde in a mixture of 20 ml of glacial acetic acid and 1 g of acetic anhydride is kept at 80° for 12 hours. The reaction mixture is introduced into 200 ml of water and the dyestuff is gradually precipitated by adding 20 g of sodium chloride and purified by reprecipitation from water/sodium chloride solution in the presence of charcoal.

The dyestuff obtained, of the formula

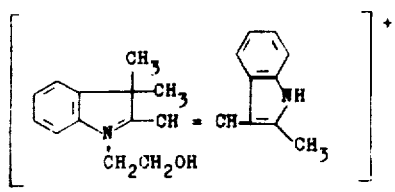

dyes fabrics of polyacrylonitrile in orange-coloured shades.

If the starting components listed in the table which follows are used for the condensation, and the procedure indicated in Example 17 is followed, dyestuffs are obtained which dye fabrics of polyacrylonitrile in the colour shades indicated.

| Indole Derivative | Oxazoloindole Derivative | Colour shade |
|---|---|---|
| 2-methylindole-3-aldehyde | according to Example 4 | orange |
| 2-methylindole-3-aldehyde | according to Example 9 | bluish-tinged red |
| 2-methylindole-3-aldehyde | according to Example 8 | orange |
| 2-methylindole-3-aldehyde | according to Example 6 | orange |
| 1,2-dimethylindole-3-aldehyde | according to Example 7 | orange |
| 2-p-tolylindole-3-aldehyde | according to Example 1 | orange |
| 2-p-tolylindole-3-aldehyde | according to Example 9 | bluish-tinged red |
| 2-p-tolylindole-3-aldehyde | according to Example 4 | orange |
| 2-p-tolylindole-3-aldehyde | according to Example 7 | orange |
| 1-methyl-2-p-tolylindole-3-aldehyde | according to Example 9 | violet |
| 1-ethyl-2-methyl-6,7-benzoindole-3-aldehyde | according to Example 1 | bluish-tinged red |
| 1-ethyl-2-methyl-6,7-benzoindole-3-aldehyde | according to Example 9 | violet |

EXAMPLE 20

2.1 g of the substance obtained according to Example 1 and 3.8 g of 1,3,3-trimethyl-2-formylmethyleneindoline in 20 ml of glacial acetic acid are heated to 110° for 5 hours. The reaction mixture is poured into 150 ml of 20% strength sodium chloride solution whilst stirring and the product is purified by reprecipitation from water/sodium chloride solution. The dyestuff obtained corresponds to the formula

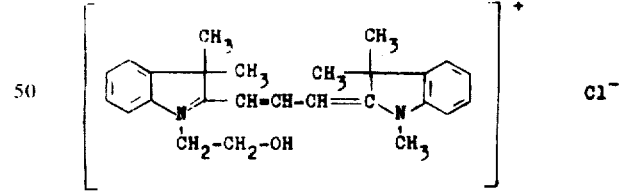

and dyes fabrics of polyacrylonitrile in bluish-tinged red shades.

If the starting components listed in the table which follows are used for the condensation and the procedure indicated in Example 19 is followed, dyestuffs are obtained which dye materials of polyacrylonitrile in the colour shades indicated.

| Aldehyde Component | Oxazoloindole derivative | Colour shade |
|---|---|---|
| 5-chloro-1,3,3-trimethyl-2-formylmethyleneindoline | according to Example 1 | bluish-tinged red |
| 1,3,3,5-tetramethyl-2-formylmethyleneindoline | according to Example 1 | bluish-tinged red |
| 5-nitro-1,3,3-trimethyl-2-formylmethylene | according to Example 1 | strongly bluish-tinged red |
| 5-nitro-1,3,3-trimethyl-2-formylmethyleneindoline | according to Example 7 | strongly bluish- |

| Aldehyde Component | -continued<br>Oxazoloindole derivative | Colour shade |
|---|---|---|
| 5-carbomethoxy-1,3,3-trimethyl-2-formylmethyleneindoline | according to Example 1 | tinged red<br>strongly bluish-tinged red |
| 1,3,3-trimethyl-2-formylmethyleneindoline | according to Example 4 | bluish-tinged red |
| 5-chloro-1,3,3-trimethyl-2-formylmethyleneindoline | according to Example 4 | bluish-tinged red |
| 5-chloro-1,3,3-trimethyl-2-formylmethyleneindoline | according to Example 7 | bluish-tinged red |
| 5-chloro-1,3,3-trimethyl-2-formylmethyleneindoline | according to Example 12 | bluish-tinged red |
| 5-chloro-1,3,3-trimethyl-2-formylmethyleneindoline | according to Example 9 | strongly bluish-tinged red |
| 1,3,3-trimethyl-2-formylmethyleneindoline | according to Example 9 | strongly bluish-tinged red |
| 1,3,3,5-tetramethyl-2-formylmethyleneindoline | according to Example 9 | strongly bluish-tinged red |
| 5-methoxy-1,3,3-trimethyl-2-formylmethyleneindoline | according to Example 9 | very strongly bluish-tinged red |
| 5-methoxy-1,3,3-trimethyl-2-formylmethyleneindoline | according to Example 1 | strongly bluish-tinged red |
| 1,3,3,5-tetramethyl-2-formylmethyleneindoline | according to Example 11 | strongly bluish-tinged red |
| 1,3,3-trimethyl-2-formylmethyleneindoline | according to Example 10 | bluish-tinged red |
| 1,3,3-trimethyl-2-formylmethyleneindoline | according to Example 12 | bluish-tinged red |
| 1,3,3-trimethyl-2-formylmethyleneindoline | according to Example 13 | bluish-tinged red |
| 5-chloro-1,3,3-trimethyl-2-formylindoline | according to Example 12 | bluish-tinged red |

I claim:

1. Methine dyestuff of the formula

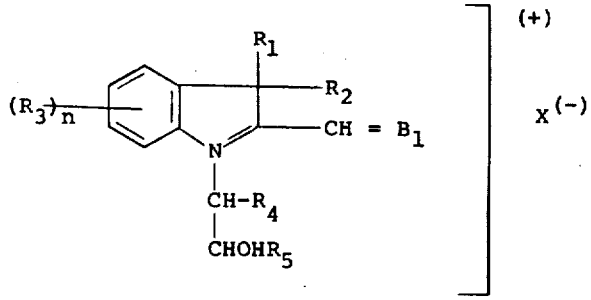

in which $R_1$ and $R_2$ are $C_1$–$C_4$-alkyl;

$R_3$ is hydrogen, a non-ionic substituent, carboxyl, or together with the ring, to which it is attached, a benzene ring;

$n$ is 1, 2, 3 or 4;

$R_4$ and $R_5$ are hydrogen or a non-ionic substituent;

$X^{(-)}$ is an anion;

said non-ionic substituents selected from the group consisting of $C_1$–$C_9$ alkyl, chloromethyl, $C_1$–$C_{12}$-alkoxymethyl, phenoxymethyl, p-nitrophenoxymethyl, p-methoxyphenoxy, p-chlorophenoxymethyl, allyloxymethyl, propargyloxymethyl, hydroxymethyl, di-$C_1$–$C_4$-alkylaminomethyl, diallylaminomethyl, pyrrolidinomethyl, phthalimidomethyl, allyl, trifluoromethyl, phenyl, benzyl, cyclohexyl, $C_1$–$C_4$-alkoxy, sulfamoyl, CN, carbomethoxy, carboethoxy, fluorine, chlorine, methylmercapto, methylsulfonyl and acetylamino;

$B_1$ is CH — $Ar_1$ or

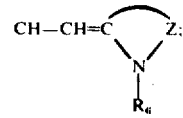

Z together with C and N to which it is attached, forms an indolinyl-2-ring;

$Ar_1$ is a radical of the p-amino-benzene, naphthalene; benzofurane, benzothiophene, indole, indoline, 1,2,3,4-tetrahydroquinoline, carbazole, quinoxaline, dihydro-[benzo-1,4-oxazine], dihydro-[benzo-1,4-thiazine], 9,10-dihydro-phenazine, phenoxazine or phenthiazine series;

$R_6$ is methyl, ethyl or benzyl.

2. Methine dyestuff of claim 1 wherein

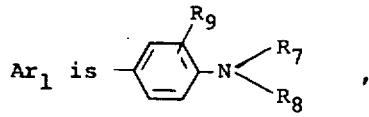

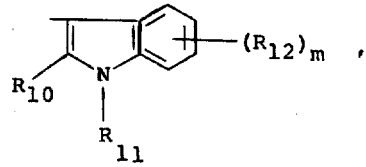

or

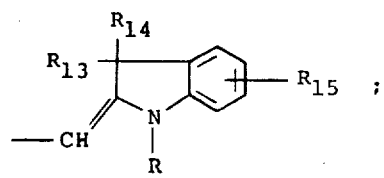

$R_7$ and $R_8$ are independently of one another hydrogen; $C_1$–$C_4$-alkyl; ethyl substituted by chlorine, cyano, or dimethylamino; cyclohexyl; phenyl; phenyl substituted by methyl; ethyl, methoxy, ethoxy or chlorine; benzyl; or $R_7$, $R_8$ together with N atom form a morpholino or piperidino radical;

$R_9$ is hydrogen or methyl; or $R_9$ which is bonded to the o-position of N, together with $R_7$ and the phenylring forms a carbazol or tetrahydrocarbazol ring system;

$R_{10}$ is hydrogen; methyl; phenyl; or phenyl substituted by chlorine or methyl;

$R_{11}$ is hydrogen; methyl or ethyl;

$R_{12}$ is hydrogen; methyl; ethyl; methoxy; chlorine or nitro;

$m$ is 1 or 2;

$R_{13}$ is methyl, ethyl, or n-propyl;

$R_{14}$ is methyl, ethyl, or n-propyl;

$R_{15}$ is hydrogen; $C_1$–$C_4$-alkyl; fluorine; chlorine; trifluoromethyl; cyclohexyl; benzyl; methoxy; ethoxy; methylmercapto; ethylmercapto; methylsulfonyl; phenoxy; methoxycarbonyl; ethoxycarbonyl; sulphamoyl; nitro; amino; acetamino; carboxyl; cyano, or together with the ring to which it is attached, forms a benzene ring.

3. Methine dyestuff of claim 1 in which $B_1$ is CH — $Ar_1$.

4. Methine dyestuff of claim 1 in which $B_1$ is

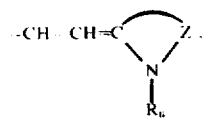

5. Methine dyestuff of claim 1 having the formula

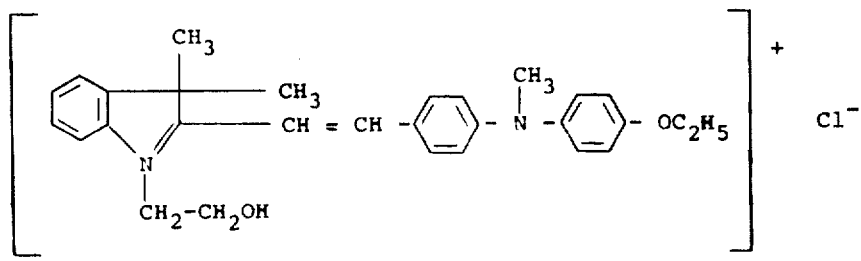

6. Methine dyestuff of claim 1 having the formula

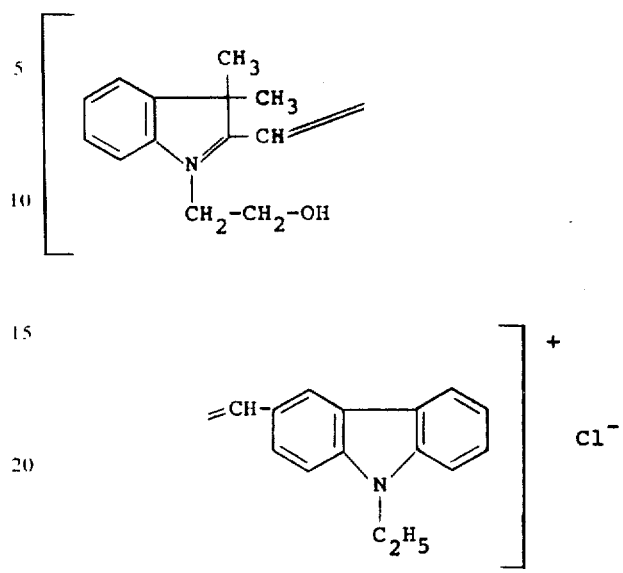

7. Methine dyestuff of claim 1 having the formula

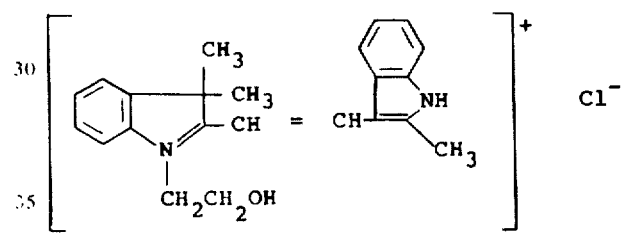

* * * * *